US009696321B2

(12) United States Patent
Kuroda et al.

(10) Patent No.: US 9,696,321 B2
(45) Date of Patent: Jul. 4, 2017

(54) THERAPEUTIC AGENT, METHOD OF TREATMENT AND METHOD FOR PREDICTING THE SEVERITY OF SYSTEMIC INFLAMMATORY RESPONSE SYNDROME (SIRS), DISEASES CAUSED OR ACCOMPANIED BY NEUTROPHIL ACTIVATION

(71) Applicant: National University Corporation Okayama University, Okayama-shi, Okayama (JP)

(72) Inventors: Kosuke Kuroda, Okayama (JP); Hiroshi Morimatsu, Okayama (JP); Hidenori Wake, Okayama (JP); Shuji Mori, Okayama (JP); Masahiro Nishibori, Okayama (JP); Hideo Takahashi, Okayama (JP); Keyue Liu, Okayama (JP); Kiyoshi Teshigawara, Okayama (JP); Masakiyo Sakaguchi, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 14/995,679

(22) Filed: Jan. 14, 2016

(65) Prior Publication Data
US 2016/0146835 A1 May 26, 2016

Related U.S. Application Data

(63) Continuation-in-part of application No. 14/406,191, filed as application No. PCT/JP2013/064779 on May 28, 2013, now Pat. No. 9,504,731.

(30) Foreign Application Priority Data

Jun. 6, 2012 (JP) ................. 2012-129232

(51) Int. Cl.
*A61K 38/00* (2006.01)
*G01N 33/68* (2006.01)

(52) U.S. Cl.
CPC ..... *G01N 33/6893* (2013.01); *G01N 2800/24* (2013.01); *G01N 2800/26* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 7,205,392 B2 | 4/2007 | Olsson et al. |
| 7,662,388 B2 | 2/2010 | Welsh et al. |
| 2005/0042201 A1 | 2/2005 | Olsson et al. |
| 2015/0141322 A1 | 5/2015 | Nishibori et al. |

FOREIGN PATENT DOCUMENTS

| JP | 2004-527242 A | 9/2004 |
| JP | 2007-528710 A | 10/2007 |
| WO | 2011123041 A1 | 10/2011 |

OTHER PUBLICATIONS

Poon et al. Biochem. J. (2009) 424, pp. 27-37.*
Extended European Search Report issued in corresponding European Patent Application No. 138011382 dated Feb. 10, 2016 (10 pages).
Manderson et al., "Interactions of histidine-rich glycoprotein with immunoglobulins and proteins of the complement system," Molecular Immunology, vol. 46, 2009, pp. 3388-3398.
Czura, et al.; J. Infect. Dis. (2003) 187 (Supplement 2): S391-S396.
International Search Report mailed Jul. 23, 2013 in International Application No. PCT/JP2013/064779.
Kirschenbaum, Linda et al., "Importance of Platelets and Fibrinogen in Neutrophil-endothelial Cell Interactions in Septic Shock," Critical Care Medicine, 2004, vol. 32, No. 9, pp. 1904-1909.
Poon, Ivan K.H. et al., "Histidine-rich Glycoprotein: The Swiss Army Knife of Mammalian Plasma," Blood, 2011, vol. 117, No. 7, pp. 2093-2101.
Rheologic.
Rydengard, Victoria et al., "Histidine-rich Glycoprotein Protects from Systemic Candida Infection," PLOS Pathogens, 2008, vol. 4, No. 8, pp. E1000116.
Shannon, Oonagh et al., "Histidine-rich Glycoprotein Promotes Bacterial Entrapment in Clots and Decreases Mortality in a Mouse Model of Sepsis," Blood, 2010, vol. 116, No. 13, pp. 2365-2372.
Tsuchida-Straeten, N. et al., "Enhanced Blood Coagulation and Fibrinolysis in Mice Lacking Histidine-rich Glycoprotein (HRG)," Journal of Thrombosis and Haemostasis, 2005, vol. 3, No. 5, pp. 865-872.
Vu, et al.; Journal of Biological Chemistry, vol. 286, No. 35; 2011; pp 30314-30323.
Vu, Trang T. et al., "Histidine-rich Glycoprotein Binds Fibrin(ogen) with High Affinity and Competes with Thrombin for Binding to the Gamma'-chain," Journal of Biological Chemistry, 2011, vol. 286, No. 35, pp. 30314-30323.

* cited by examiner

*Primary Examiner* — Jeanette Lieb
(74) *Attorney, Agent, or Firm* — Kilyk & Bowersox, P.L.L.C.

(57) ABSTRACT

The present invention provides a neutrophil activation regulator comprising a histidine-rich glycoprotein (HRG) for the treatment of systemic inflammatory response syndrome (SIRS), diseases caused by neutrophil activation and/or inflammatory diseases accompanied by neutrophil activation in a subject in need thereof. Further, the present invention provides methods for predicting the severity of systemic inflammatory response syndrome (SIRS), diseases caused by neutrophil activation and/or inflammatory diseases accompanied by neutrophil activation in a subject in need thereof, and methods for predicting the survival of a subject with systemic inflammatory response syndrome (SIRS), diseases caused by neutrophil activation and/or inflammatory diseases accompanied by neutrophil activation, that comprise determining the blood level of histidine-rich glycoprotein in the subject.

16 Claims, 24 Drawing Sheets

FIGURE 1
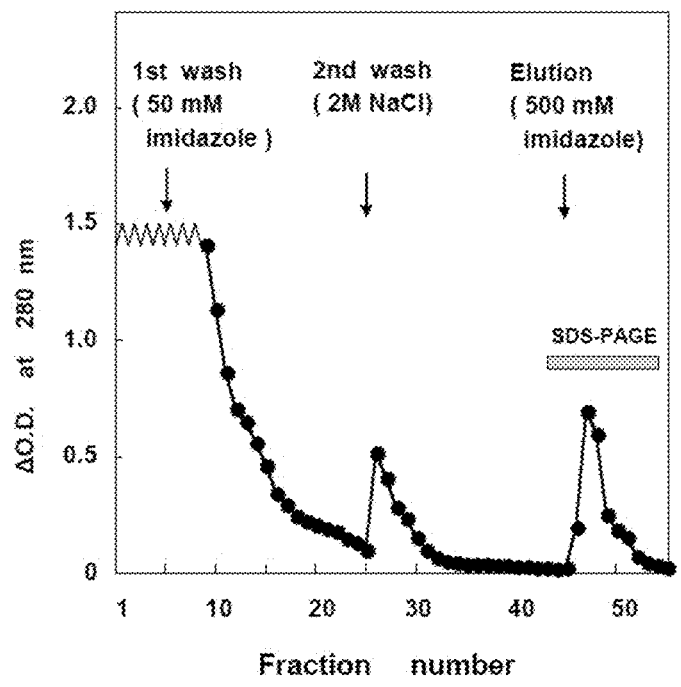
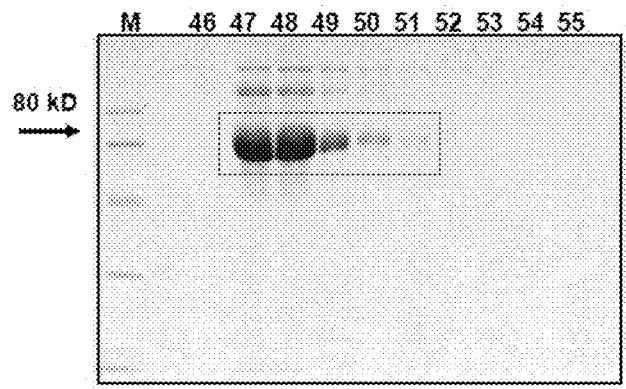

The HRG did not enhance horizontal migration.

Horizontal migration was enhanced.

FIGURE 11
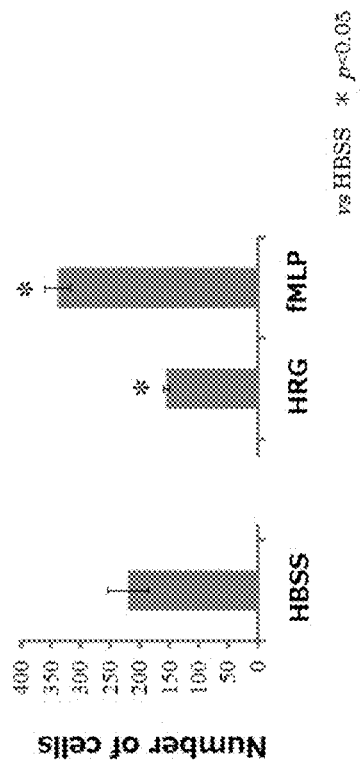
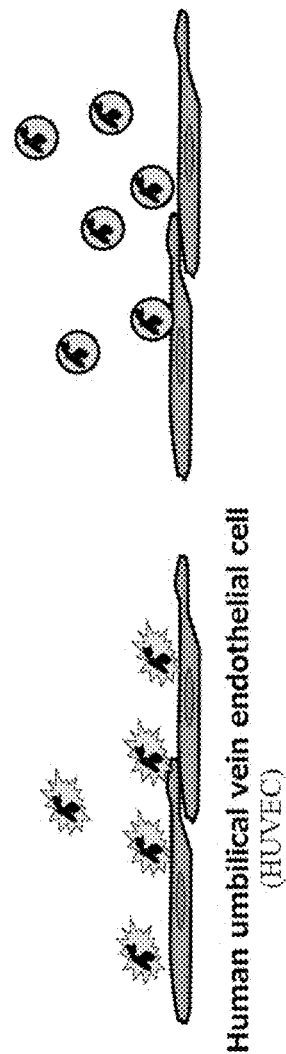

THERAPEUTIC AGENT, METHOD OF TREATMENT AND METHOD FOR PREDICTING THE SEVERITY OF SYSTEMIC INFLAMMATORY RESPONSE SYNDROME (SIRS), DISEASES CAUSED OR ACCOMPANIED BY NEUTROPHIL ACTIVATION

CROSS-REFERENCE TO RELATED APPLICATION

Japan Priority Application 2012-129232, filed Jun. 6, 2012, including the specification, drawings, claims and abstract, is incorporated herein by reference in its entirety. This application is a Continuation-In-Part of U.S. application Ser. No. 14/406,191 filed Dec. 5, 2014 which is the National Stage of PCT/JP2013/064779, filed May 28, 2013. All of the aforesaid applications are incorporated herein by reference in their entirety.

The instant application contains a Sequence Listing which has been submitted in ASCII format via EFS-WEB and is hereby incorporated by reference in its entirety. Said ASCII copy created on Nov. 20, 2014, is named sequence.txt and is 5 KB.

FIELD OF THE INVENTION

The present invention relates to a neutrophil activation regulator comprising a histidine-rich glycoprotein (HRG) for the treatment of systemic inflammatory response syndrome (SIRS), diseases caused by neutrophil activation and/or inflammatory diseases accompanied by neutrophil activation in a subject in need thereof. Further, the present invention provides methods for predicting the severity of systemic inflammatory response syndrome (SIRS), diseases caused by neutrophil activation and/or inflammatory diseases accompanied by neutrophil activation in a subject in need thereof, and methods for predicting the survival of a subject with systemic inflammatory response syndrome (SIRS), diseases caused by neutrophil activation and/or inflammatory diseases accompanied by neutrophil activation, that comprise determining the blood level of histidine-rich glycoprotein in the subject.

BACKGROUND OF THE INVENTION

Blood includes erythrocytes, leukocytes and platelets as cell components. Among them, the leukocytes are classified into five categories: granulocytes (neutrophil, eosinophil and basophil), lymphocytes and monocytes. The neutrophils are the greatest number of cell types in human, and are well known to function on the front line of biological defense against bacterial infection, histological damage, and the like. The neutrophils are activated by bacterial cell components (e.g. lipopolysaccharide: LPS), bacteria-derived peptide, complement C5a, IL-8, and the like. The neutrophil is one of main ingredients of granulocytes in leucocytes, and when a foreign substance like bacteria enters a living body, the neutrophil migrates to its site and phagocytizes a foreign substance such as bacteria to generate active oxygen. Furthermore, the neutrophil plays an important role in release of bactericidal proteins such as lysozyme and defensin (de-granulation) and elimination of foreign substances by actions of the proteins as well as various acidic hydrolase, or the like. However, if this active oxygen and the bactericidal proteins are excessively released outside the cells, they cause tissue damages, and optionally worsen an acute inflammation caused by entrance of foreign substances. Furthermore, in cases of particular diseases such as acute pulmonary disorder, acute respiratory distress syndrome and other neutrophil-related inflammations, this action of the neutrophil is known to have adverse effects on diseases.

Neutrophil elastase is a neutral protease having a molecular weight of about 30,000 and present in azurophil granule (lysosome). In a physiological state, in the neutrophil, the neutrophil elastase digests and degrades a phagocytized bacterium and foreign substance, and on the outside of the neutrophil, degrades elastin, collagen (types III and IV), fibronectin, immunoglobulin, blood coagulation factor XIII, etc. to regulate tissue biosynthesis. When the neutrophil elastase is excessively released and inhibitors such as $\alpha$1-AT ($\alpha$1-antitrypsin) are deficient, it may degrade even biological constituents and cause its own tissue damage. In inflammation, the neutrophil infiltrates into an inflammatory lesion, but conversely there is an aspect in which inflammation is caused by a substance produced by leukocyte like elastase. Recently, particularly in clinical sites, the kinetics of the neutrophil elastase and various diseases have attracted attentions. The neutrophil elastase has potent and broad degradation ability for proteins, and since it degrades particularly collagen, elastin, proteoglycan, etc. which are extracellular matrix components, it had been considered as one of factors of histological damages. Thus, medicines focusing to inhibitory effects of the neutrophil elastase are being developed. For example, there is a report that an H2 receptor antagonist, ranitidine hydrochloride (Name of drug: Zantac) decreases an intracellular $Ca^{2+}$ concentration of the neutrophil and reduces release of the neutrophil elastase. In addition, sivelestat sodium (Name of drug: Elaspol) is a specific inhibitor for elastase released from the neutrophil out of the cell, and also a therapeutic agent which has a license to be applied to respiratory distress syndrome and acute pulmonary disorder in Japan. These drugs are not essentially drugs which inhibit activation of the neutrophil, but work on only one factor released by the activated neutrophil to inhibit its enzyme activity, and thus its anti-inflammatory action is expected.

Although there is a report about a substance which acts on a factor released an activated neutrophil and inhibits its activity as mentioned above, an inhibitory mechanism of the neutrophil is largely unknown. Particularly, for preventing runaway activation of the neutrophil in the circulation, the neutrophil should be kept in an inactive state. However, there has been no report about a factor capable of maintaining/regulating the neutrophil in an inactive state.

HRG (Histidine-rich glycoprotein) is a plasma protein with a molecular weight of about 80 kDa which was identified by Heimburger et al. in 1972. HRG is a high histidine-containing protein made up of a total of 507 amino acids in which 66 histidines are contained, and is mainly synthesized in a liver and contained in human plasma at a concentration as extremely high as about 100-150 μg/ml. HRG is known to be involved in regulation of a coagulation fibrinolysis system and control of angiogenesis (Blood, Vol. 117, No. 7, 2093-2101 (2011)). Furthermore, a method for inhibiting angiogenesis by administration of a HRG polypeptide, and a pharmaceutical composition and a product which comprising the HRG polypeptide, an antibody and receptor binding to the HRG polypeptide, a HRG-deficient plasma and polynucleotide, a HRG polypeptide-coding vector and a host cell are disclosed (JP 2004-527242 A). Additionally, in relation to the field of angiogenesis, there is a disclosure relating to the use of a substantially-pure continuous polypeptide with an anti-angiogenesis activity containing a sub-fragment derived from a central area of the HRG (JP 2007-528710 A).

However, there has been no report about effects of the HRG on control of the neutrophil.

Traditionally, the systemic response to infection has been termed sepsis, and it is considered an increasingly common cause of morbidity and mortality, especially in the elderly. Immunocompromised ad critically ill patients. However, a systemic response can occur even in the absence of an infection, in association with several clinical conditions. Non-infectious pathologic causes may include pancreatitis, ischemia, multiple trauma and tissue injuries, hemorrhagic shock, immune-mediated organ injury, and the administration of inflammatory mediators, such as cytokines, for example the tumor necrosis factor. The systemic response may include more than one of the following clinical manifestations: (1) a body temperature greater than 38° C. or less than 36° C.; (2) a heart rate greater than 90 beats per minute; tachypnea, manifested by a respiratory rate greater than 20 breaths per minute, or hyperventilation, as indicated by an arterial carbon dioxide tension ($PaCO_2$) of less than 32 mm Hg; and an abnormal count of white blood cells, such as a count greater than 12,000 µl or less than 4,000 µl.

In 1992, the American College of Chest Physicians (ACCP) and the Society of Critical Care Medicine (SCCM) proposed the phrase "systemic inflammatory response syndrome" (SIRS), to describe the inflammatory process independent of its cause. The ACCP and the SCCM further classified SIRS into sepsis, severe sepsis, septic shock, and multiple organ dysfunction syndrome (MODS). When SIRS is the result of a confirmed infection, it is termed "sepsis." Severe sepsis is defined as sepsis associated with organ dysfunction, abnormal hypo-perfusion, or sepsis-induced hypotension. Septic shock is a subset of severe sepsis, and is defined as sepsis-induced hypotension, which persists despite adequate fluid resuscitation, along with the presence of hypo-perfusion abnormalities or organ dysfunction. MODS is a pattern of multiple and progressive symptoms and signs that are pathogenetically related. The idea behind the classification of SIRS was to identify the pathogenic mechanisms involved in the systemic inflammatory response.

Infection is defined as "a microbial phenomenon characterized by an inflammatory response to the microorganisms or the invasion of normally sterile tissue by those organisms." Bacteremia, a condition characterized by the presence of bacteria within the bloodstream, does not always lead to SIRS or sepsis. Sepsis-induced hypotension is defined as "the presence of a systolic blood pressure of less than 90 mm Hg or a reduction of more than 40 mm Hg from baseline in the absence of other causes of hypotension." Patients meet the criteria for septic shock if they have persistent hypotension and perfusion abnormalities despite adequate fluid resuscitation.

Possible complications may include respiratory failure, acute respiratory distress syndrome (ARDS), and nosocomial pneumonia, renal failure, gastrointestinal (GI) bleeding and stress gastritis, anemia, deep vein thrombosis (DVT), intravenous catheter-related bacteremia, electrolyte abnormalities, hyperglycemia and disseminated intravascular coagulation (DIC). SIRS is considered by many as a self-defense mechanism, where inflammation is the body's response to insults from chemical, traumatic or infectious stimuli. Trauma, inflammation, or infection leads to the activation in SIRS of an inflammatory cascade with increased systemic expression of a first pro-inflammatory response, and a later anti-inflammatory response. When SIRS is mediated by an infectious insult, the inflammatory cascade is often initiated by endotoxin or exotoxin. Tissue macrophages, monocytes, mast cells, platelets, and endothelial cells produce cytokines. The release of tissue necrosis factor-alpha (TNF-α) and interleukin-1 (IL-1) leads to cleavage of the nuclear factor-kB (NF-kB) inhibitor, which in turn initiates the production of mRNA, with consequent production of more pro-inflammatory cytokines, such as IL-6, IL-8, and interferon gamma. The release of TNF-α and IL-1 produces fever and the release of stress hormones, such as norepinephrine, vasopressin, activation of the renin-angiotensin-aldosterone system. Release of TNF-α is greater in inflammation than in trauma. IL-6, stimulates the release of acute-phase reactants such as C-reactive protein (CRP) and pro-calcitonin.

Pro-inflammatory interleukins may function directly on tissue or act through secondary mediators to activate the coagulation cascade, the complement cascade and the release of nitric oxide, platelet-activating factor, prostaglandins, and leukotrienes. IL-1 and TNF-α also directly affect endothelial surfaces, leading to the expression of tissue factor, which in turn initiates the production of thrombin and the process of coagulation. Fibrinolysis is impaired by IL-1 and TNF-α via production of plasminogen activator inhibitor-1. Pro-inflammatory cytokines also disrupt the naturally occurring anti-inflammatory mediators anti-thrombin and activated protein-C (APC). If untreated, the coagulation cascade leads to complications, including microvascular thrombosis and organ dysfunction.

To counteract the acute inflammatory response, the body activates the counter-inflammatory response syndrome (CARS). IL-4 and IL-10 are cytokines responsible for decreasing the production of TNF-α, IL-1, IL-6, and IL-8. The acute phase response also produces antagonists to TNF-α and IL-1 receptors, which either bind and inactivate the cytokine, a or block the receptors. Comorbidities and other factors can influence a patient's ability to respond appropriately. The balance of SIRS and CARS helps determine a patient's outcome after an insult.

Infectious causes of SIRS include, but are not limited to, bacterial sepsis, burn wound infections, candidiasis, cellulitis, cholecystitis, community-acquired pneumonia, diabetic foot infection, erysipelas, infective endocarditis, influenza, intra-abdominal infections, such as diverticulitis and appendicitis, gas gangrene, meningitis, nosocomial pneumonia, pseudomembranous colitis, pyelonephritis, septic arthritis, toxic shock syndrome, and urinary tract infections.

Noninfectious causes of SIRS include, but are not limited to, acute mesenteric ischemia, adrenal insufficiency, autoimmune disorders, burns, chemical aspiration, cirrhosis, cutaneous vasculitis, dehydration, drug reaction, electrical injuries, erythema multiforme, hemorrhagic shock, hematologic malignancy, intestinal perforation, medication side effect, for example, from theophylline, myocardial infarction, pancreatitis, seizure, substance abuse, stimulants, such as cocaine and amphetamines, surgical procedures, toxic epidermal necrolysis, transfusion reactions, upper gastrointestinal bleeding and vasculitis.

The sex-based mortality risk of severe SIRS is unknown. Females tend to have less inflammation from the same degree of pro-inflammatory stimuli because of the mitigating aspects of estrogen. The mortality rate among women with severe sepsis is similar to that of men who are 10 years younger; however, whether this protective effect applies to women with noninfectious SIRS is unknown. Prognosis depends on the etiologic source of SIRS, as well as on associated comorbidities. The mortality rates may vary depending on the causes of SIRS, any complications of organ failure that may occur, and the length of the hospital stay.

Systemic inflammatory response syndrome (SIRS) is a very common disease, although not all patients with SIRS require hospitalization or have diseases that progress to serious illness, since SIRS criteria are nonspecific and occur in patients who present a variety of conditions. Therefore, it is important to determine the severity of SIRS. To date, no reliable method has been developed that reliably predict the severity of SIRS. The present invention overcomes the deficiencies of the prior art, by providing reliable methods for predicting the severity of systemic inflammatory response syndrome (SIRS), diseases caused by neutrophil activation and/or inflammatory diseases accompanied by neutrophil activation in a subject in need thereof.

SUMMARY OF THE INVENTION

An object of the present invention is to provide a neutrophil activation regulator comprising a histidine-rich glycoprotein (HRG) for the treatment of systemic inflammatory response syndrome (SIRS), diseases caused by neutrophil activation and/or inflammatory diseases accompanied by neutrophil activation in a subject in need thereof. An additional object of the present invention is to provide methods for predicting the severity of systemic inflammatory response syndrome (SIRS), diseases caused by neutrophil activation and/or inflammatory diseases accompanied by neutrophil activation in a subject in need thereof. It is yet another object of the present invention to provide methods for predicting the survival of a subject with systemic inflammatory response syndrome (SIRS), diseases caused by neutrophil activation and/or inflammatory diseases accompanied by neutrophil activation, that comprise determining the blood level of histidine-rich glycoprotein in the subject.

In accordance with the objects of the present invention, and as a result of earnest investigations by the inventors, in one embodiment the present application provides a method for determining the severity of a systemic inflammatory response syndrome (SIRS) in a subject in need thereof, that comprises collecting a blood sample from the subject, separating and purifying a plasma-enriched fraction from the blood and measuring the level of histidine-rich glycoprotein in the plasma-enriched fraction. In one aspect of the invention, a level of histidine-rich glycoprotein below 30 µg/ml in the plasma-enriched fraction indicates severe systemic inflammatory response syndrome (SIRS) in the subject. In another aspect of the invention, the level of histidine-rich glycoprotein in the plasma-enriched fraction that indicates severe systemic inflammatory response syndrome (SIRS) in the subject is between 1 and 30 µg/ml. The level of histidine-rich glycoprotein in the blood of the subject may be measured by an immunological technique. The immunological technique may be quantitative ELISA, and the histidine-rich glycoprotein may be detected by Ni-NTA affinity.

In one aspect of the invention, the systemic inflammatory response syndrome (SIRS) includes, but is not limited to, one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

In another aspect of the invention, the systemic inflammatory response syndrome (SIRS) is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, hepatitis, organ dysfunction after surgical operation, acute/chronic rejection after organ transplantation, DIC, endocarditis, ischemia reperfusion disorder, myocardial infarction and congestive heart failure.

In a different embodiment, the invention provides a method for determining the severity of a disease caused by neutrophil activation and/or an inflammatory disease accompanied by neutrophil activation in a subject in need thereof, comprising collecting a blood sample from the subject, separating and purifying a plasma-enriched fraction from the blood and measuring the level of histidine-rich glycoprotein in the plasma-enriched fraction. In one aspect of the invention, a level of histidine-rich glycoprotein below 30 µg/ml in the plasma-enriched fraction indicates a severe disease caused by neutrophil activation and/or an inflammatory disease accompanied by neutrophil activation in the subject. In another aspect of the invention, the level of histidine-rich glycoprotein in the plasma-enriched fraction that indicates a severe disease caused by neutrophil activation and/or an inflammatory disease accompanied by neutrophil activation in the subject is between 1 and 30 µg/ml.

The level of histidine-rich glycoprotein in the blood of the subject may be measured by an immunological technique. The immunological technique may be quantitative ELISA, and the histidine-rich glycoprotein may be detected by Ni-NTA affinity.

In one aspect of the invention, the disease caused by neutrophil activation and/or an inflammatory disease accompanied by neutrophil activation includes, but is not limited to, one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

In yet another aspect of the invention, the disease caused by neutrophil activation and/or an inflammatory disease accompanied by neutrophil activation is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, hepatitis, organ dysfunction after surgical operation, acute/chronic rejection after organ transplantation, DIC, endocarditis, ischemia reperfusion disorder, myocardial infarction and congestive heart failure.

In yet another embodiment, the invention provides a method for predicting the survival of a subject with systemic inflammatory response syndrome (SIRS) comprising collecting a blood sample from the subject, separating and purifying a plasma-enriched fraction from the blood and measuring the level of histidine-rich glycoprotein in the plasma-enriched fraction, wherein a level of histidine-rich glycoprotein below 30 µg/ml in the plasma-enriched fraction indicates poor survival of the subject. In another aspect of the invention, the level of histidine-rich glycoprotein in the plasma-enriched fraction that indicates poor survival of the subject is between 1 and 30 µg/ml.

The level of histidine-rich glycoprotein in the blood of the subject may be measured by an immunological technique. The immunological technique may be quantitative ELISA, and the histidine-rich glycoprotein may be detected by Ni-NTA affinity.

In one aspect of the invention, the systemic inflammatory response syndrome (SIRS) includes, but is not limited to, one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

In another aspect of the invention, the systemic inflammatory response syndrome (SIRS) is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, hepatitis, organ dysfunction after surgical operation, acute/chronic rejection after organ transplantation, DIC, endocarditis, ischemia reperfusion disorder, myocardial infarction and congestive heart failure.

In a different embodiment, the invention provides a method for predicting the survival of a subject with a disease caused by neutrophil activation and/or an inflammatory disease accompanied by neutrophil activation comprising collecting a blood sample from the subject, separating and purifying a plasma-enriched fraction from the blood and measuring the level of histidine-rich glycoprotein in the plasma-enriched fraction, wherein a level of histidine-rich glycoprotein below 30 µg/ml in the plasma-enriched fraction indicates poor survival of the subject. In another aspect of the invention, the level of histidine-rich glycoprotein in the plasma-enriched fraction that indicates poor survival of the subject is between 1 and 30 µg/ml.

The level of histidine-rich glycoprotein in the blood of the subject may be measured by an immunological technique. The immunological technique may be quantitative ELISA, and the histidine-rich glycoprotein may be detected by Ni-NTA affinity.

In one aspect of the invention, the disease caused by neutrophil activation and/or an inflammatory disease accompanied by neutrophil activation includes, but is not limited to, one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

In a different aspect of the invention, the disease caused by neutrophil activation and/or an inflammatory disease accompanied by neutrophil activation is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, hepatitis, organ dysfunction after surgical operation, acute/chronic rejection after organ transplantation, DIC, endocarditis, ischemia reperfusion disorder, myocardial infarction and congestive heart failure.

ADVANTAGEOUS EFFECT OF INVENTION

The neutrophil-vascular endothelial cell interaction can be inhibited by the neutrophil activation regulator comprising the HRG of the present invention as an active ingredient, for example the regulator can be used as a therapeutic agent for the diseases caused by neutrophil activation and/or the inflammatory diseases accompanied by neutrophil activation. Furthermore, an inspection method for diseases caused by neutrophil activation can be provided by measuring the blood HRG level.

BRIEF DESCRIPTION OF THE DRAWINGS

FIG. 1 Diagrams showing results of purification of the HRG from human plasma by Nickel-nitrilotriacetic acid (Ni-NTA) affinity chromatography (Example 1).

FIG. 11 A graph and a conceptual diagram in observing adhesiveness of the neutrophil to the vascular endothelial cell when the neutrophil was treated with HRG. The positive control is fMLP, and the negative control is HBSS (Experimental Example 1-4).

DETAILED DESCRIPTION OF THE INVENTION

Figure 2:
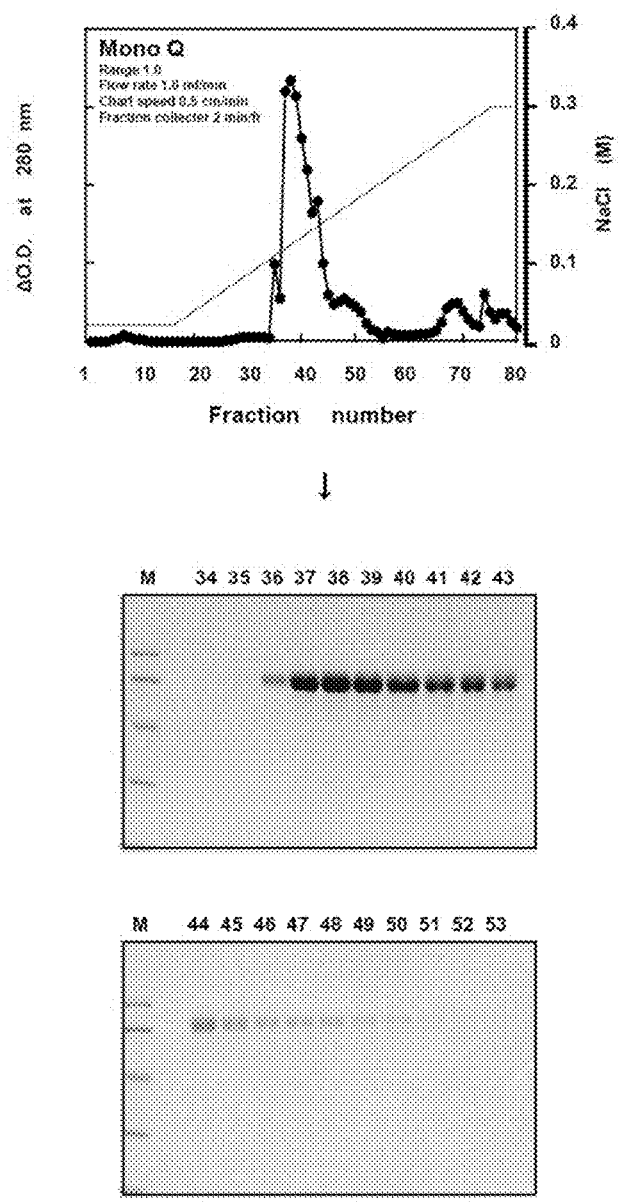
FIG. 2 Diagrams showing results of purification of the HRG from human plasma by anion-exchange chromatography (Example 1).

The present invention relates to a neutrophil activation regulator which comprising a HRG (Histidine-rich glycoprotein) as an active ingredient. In the present specification, the "HRG" as an active ingredient can be prepared from biological constituents by a method such as isolation/purification, genetic engineering technique or synthesis.

In the present specification, the HRG can be prepared from biological constituents of blood such as plasma or serum, spinal fluid, lymph, and the like by isolation/purification. Particularly, suitable biological constituents are blood components such as plasma and serum. As to the method for isolating/purifying the HRG from the biological constituents, known per se methods or any methods which will be developed in the future can be applied. For example, the HRG can be isolated/purified by allowing plasma to pass through an affinity column prepared using a Ni-NTA (nickel-nitrilotriacetic acid) agarose resin.

In the present specification, the HRG can also be prepared using a genetic engineering technique. Known per se methods or every method which will be developed in the future can be applied as the method by the genetic engineering technique. A whole-length cDNA encoding the HRG, or a cDNA encoding a site having HRG activity, for example, a whole-length cDNA encoding an amino acid sequence (SEQ ID NO: 1) of a mature HRG or a cDNA encoding its part can also be cloned in an expression vector for preparation. For example, the HRG can also be prepared from the whole or its part of a nucleotide identified in GenBank Accession No. NM000412 by a genetic engineering technique. The HRG as an active ingredient in the present invention may be the whole of the mature HRG, or a partial protein or a peptide having HRG activity in the mature HRG. Furthermore, the HRG may be a HRG with or without a sugar chain.

The amino acid sequence of the mature HRG (SEQ ID NO: 1)

VSPTDCSAVEPEAEKALDLINKRRRDGYLFQLLRIADAHLDRVENTTVYY

LVLDVQESDCSVLSRKWNDCEPPDSRRPSEIVIGQCKVIATRHSHESQDL

RVIDFNCTTSSVSSALANTKDSPVLIDFFEDTERYRKQANKALEKYKEEN

DDFASFRVDRIERVARVRGGEGTGYFVDFSVRNCPRHHFPRHPNVFGFCR

ADLFYDVEALDLESPKNLVINCEVFDPQEHENINGVPPHLGHPFHWGGHE

RSSTTKPPFKPHGSRDHHHPHKPHEHGPPPPPDERDHSHGPPLPQGPPPL

LPMSCSSCQHATFGTNGAQRHSHNNNSSDLHPHKHHSHEQHPHGHHPHAH

HPHEHDTHRQHPHGHHPHGHHPHGHHPHGHHPHGHHPHCHDFQDYGPCDP

PPHNQGHCCHGHGPPPGHLRRRGPGKGPRPFHCRQIGSVYRLPPLRKGEV

LPLPEANFPSFPLPHHKHPLKPDNQPFPQSVSESCPGKFKSGFPQVSMFF

THTFPK

After signal peptides are cleaved by a protease, the mature HRG is made up of four main regions: (1) cystatin-like region 1, (2) cystatin-like region 2, (3) His/Pro region and (4) C-terminal region. The His/Pro region is very rich in proline residues and histidine residues, and can be identified by amino acid sequences shown in position 330 to position 389 in the amino acid sequence identified by SEQ ID NO: 1. In another aspect, for example, in a human type, the His/Pro region can also be identified by amino acid sequence including about 12 tandem repeats in which a pentapeptide GHHPH (SEQ ID NO: 2) is preserved.

The "neutrophil activation regulator" of the present invention comprising the above-explained HRG as an active ingredient. The "neutrophil activation regulator" of the present invention can include a HRG obtained by isolation/purification from biological constituents or a HRG obtained by gene recombination as an active ingredient, and additionally a pharmaceutically acceptable carrier. The pharmaceutically acceptable carrier can include, for example, excipient, disintegrator or disintegrating aid, binder, lubricant, coating agent, pigment, diluent, base, solubilizer or solubilizing agent, isotonicifier, pH regulator, stabilizer, propellant, sticker, and the like. The neutrophil activation regulator in the present invention may be a crude product itself obtained from biological constituents by isolation/purification.

The neutrophil activation regulator of the present invention has an action to inhibit neutrophil activity in addition to an action to inhibit neutrophil-vascular endothelial cell interaction. Furthermore, the neutrophil activation regulator can be used for a therapeutic agent for diseases caused by neutrophil activation and/or inflammatory diseases accompanied by neutrophil activation that utilizes actions to inhibit neutrophil activity and to inhibit neutrophil-vascular endothelial cell interaction. Consequently, the present invention extends to the neutrophil-vascular endothelial cell interaction depressant agent including the neutrophil activation regulator and to the therapeutic agent for diseases caused by neutrophil activation and/or inflammatory diseases accompanied by neutrophil activation.

The present invention also extends to a treatment method for diseases caused by neutrophil activation and/or inflammatory diseases accompanied by neutrophil activation, characterized in that the neutrophil activation regulator comprising the HRG as an active ingredient is used.

The "diseases caused by neutrophil activation and/or inflammatory diseases accompanied by neutrophil activation" in the present specification may be literally any diseases caused by neutrophil activation and/or any inflammatory diseases accompanied by neutrophil activation, and include, but are not especially limited to, one or a plurality of diseases selected from, for example, sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia. Particularly, the diseases include suitably any diseases selected from sepsis, acute respiratory distress syndrome, and acute pancreatitis.

The "neutrophil-vascular endothelial cell interaction depressant agent" or "therapeutic agent for diseases caused by neutrophil activation and/or inflammatory diseases accompanied by neutrophil activation" of the present invention may be locally or systemically administered. A parenteral formulation may include a sterilized aqueous or non-aqueous solution, suspension and emulsion. Examples of non-aqueous diluent may include propylene glycol, polyethylene glycol, vegetable oil, for example, olive oil and organic ester composition, for example, ethyl oleate, and they are suitable for injection. Aqueous carriers may include water, alcoholic aqueous solution, emulsion, suspension, salt water and buffered medium. Non-aqueous carriers may include sodium chloride solution, Ringer dextrose, dextrose and sodium chloride, Ringer lactic acid and binding oil. Intravenous carrier may include, for example, filler for liquid, nutrition and electrolyte (based on, for example, Ringer dextrose). The therapeutic agent of the present invention for diseases caused by neutrophil activation and/or inflammatory diseases accompanied by neutrophil activation can further include a preservative and other additives, for example, an antimicrobial compound, an antioxidant, a chelating agent, an inert gas, and the like.

The "depressant agent for neutrophil-vascular endothelial cell interaction" or the "therapeutic agent for diseases caused by neutrophil activation and/or inflammatory diseases accompanied by neutrophil activation" of the present invention may be used in combination with other drugs. For example, an anti-HMGB1 monoclonal antibody described in a brochure of WO/2012/074043 can also be combined for use.

Furthermore, the present invention extends to an inspection method for diseases caused by neutrophil activation and/or inflammatory diseases accompanied by neutrophil activation, which is characterized in that a blood HRG level is measured. In the case of diseases caused by neutrophil activation and/or inflammatory diseases accompanied by neutrophil activation, it is recognized that the blood HRG level is inclined to be lower than the normal level. Specific examples of the diseases caused by neutrophil activation and/or the inflammatory diseases accompanied by neutrophil activation are as mentioned above.

The measurement method of the blood HRG level may be any method enabling quantitative measurement, and the level can be measured by e.g., but not particularly limited to, immunological procedure. The immunological procedure includes measurement methods using anti-HRG antibodies, and more specifically includes an antibody sandwich ELISA (Enzyme-Linked ImmunoSorbent Assay) method, an antibody/NiNTA-HRP probe sandwich ELISA method, an ELISA method using chemoluminescence for detection, a latex agglutination method, a western blot method, and the like. As a test sample subjected to these measurement methods, a sample in which a specimen obtained through blood collection by known per se method is prepared by a preparation method for conventional clinical test samples can be used. More specifically, a plasma sample prepared by, for example, a preparation method for conventional clinical test samples can be used as a test sample.

EXAMPLES

Hereinafter, the present invention will be specifically explained by Examples and Experimental Examples. Basically, the present invention is not limited by the following Examples and the like, and can be carried out with appropriate modifications within the scope that can be adapted to the gist of the present invention, and any of the modifications are incorporated in the technical scope of the present invention.

(Example 1) Preparation of Neutrophil Activation Regulator

In this Example, preparation of the neutrophil activation regulator including the HRG as an active ingredient will be explained.

In this Example, a human plasma (240 ml) was used as a starting material, and the HRG was purified by Ni-NTA (nickel-nitrilotriacetic acid) affinity chromatography and high-performance liquid chromatography (anion-exchange column (monodisperse hydrophilic polymer beads: Mono Q)). A purification pattern from the human plasma is shown in FIG. 1 and FIG. 2. Thereby, a HRG purification sample was obtained in a fraction of molecular weight of about 80 kDa. The purified sample was dialyzed by a phosphate buffered saline (1×PBS (-)), and the preparation containing 500-1000m/ml (5 ml) of HRG was stored as the neutrophil activation regulator of the present invention. For the experiment, the concentration of the HRG was adjusted by Hank's balanced salt solutions (HBSS) for use.

(Experimental Example 1-1) Confirmation of Chemotaxis by Agarose Flat Plate

The chemotaxis of the neutrophil in a horizontal state by the neutrophil activation regulator (HRG: 1 µM) prepared in Example 1 was confirmed. In this Experimental Example, an HBSS containing 5×106 cell/ml of neutrophil prepared from human peripheral blood was used as a neutrophil suspension. An HBSS containing 1 µM of bovine serum albumin (BSA) was used as a negative control, and an HBSS containing 1 µM of fMLP (bacteria-derived migratory factor: N-formyl-methionyl-leucyl-phenylalanine) was used as a positive control.

Figure 3:
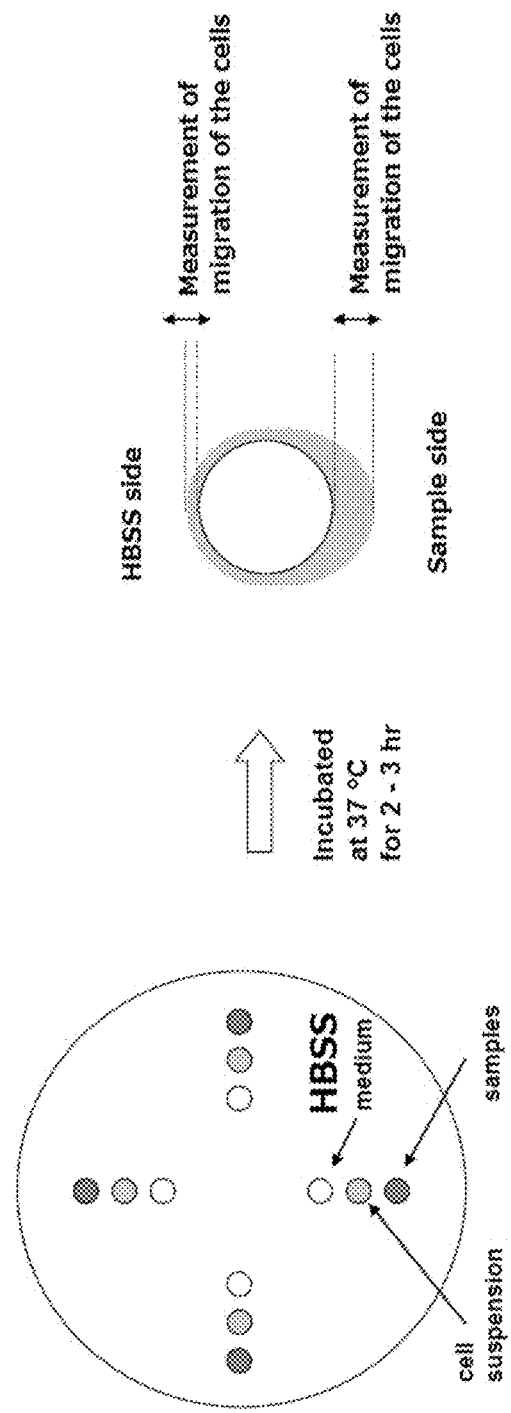
FIG. 3 Diagrams showing an assay method for migration capability of the neutrophil by agarose flat plate (Experimental Example 1-1).
Figure 4A:
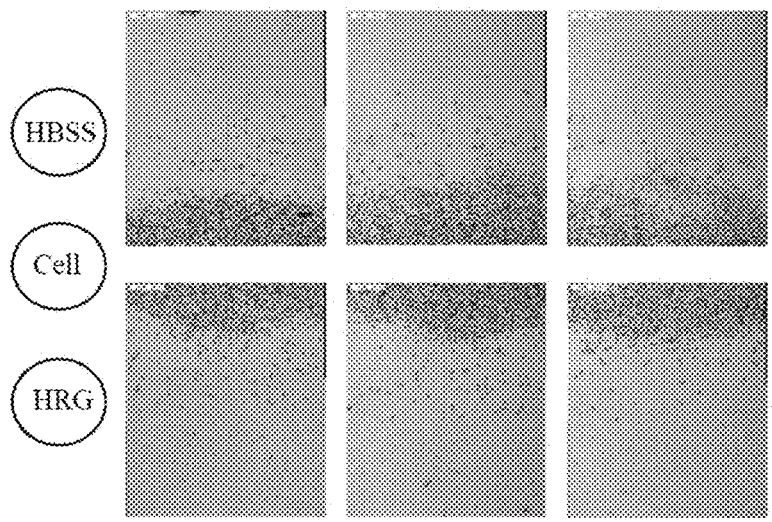
FIG. 4A Photographs taken in confirming migration capability of the neutrophil with HRG by agarose flat plate (Experimental Example 1-1).
Figure 4B:
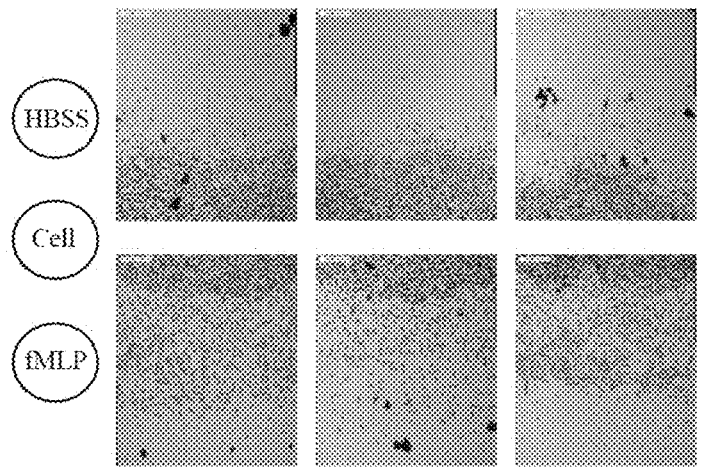
FIG. 4B Photographs taken in confirming migration capability of the neutrophil with fMLP (positive control) by agarose flat plate (Experimental Example 1-1).
Figure 4C:
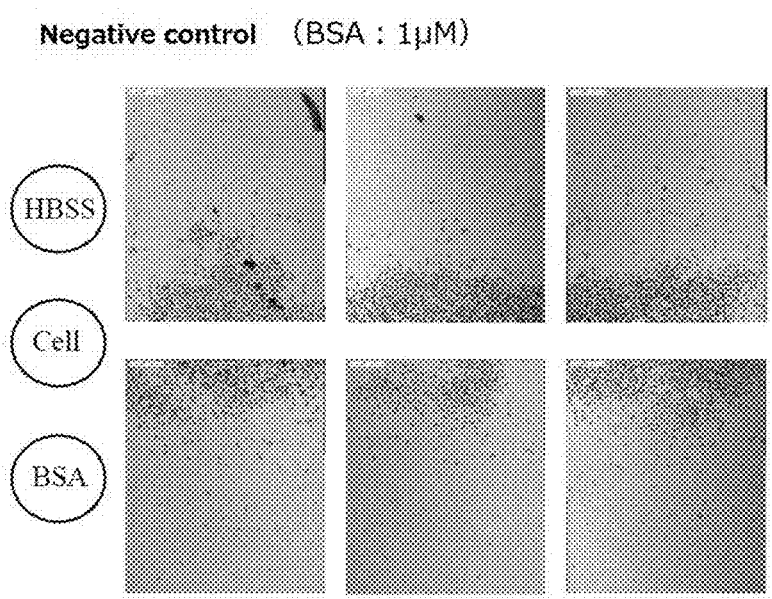
FIG. 4C Photographs taken in confirming migration capability of the neutrophil with BSA (bovine serum albumin: negative control) by agarose flat plate. (Experimental Example 1-1).

Three holes with 3 mm of diameter are provided on the agarose flat plate as shown in FIG. 3, 10 µl of HBSS was added in one hole, 10 µl of sample solution (sample) like a neutrophil activation regulator was added on the other hole, and 10 µl of neutrophil suspension was added on the middle hole. They were cultured at 37° C. for 3 hours, and migration of cells was confirmed. As a result, the system with the neutrophil activation regulator (HRG) showed no migration of neutrophil like the system of the negative control (BSA) (FIG. 4C), as shown in FIG. 4A.

(Experimental Example 1-2) Morphology of Neutrophil

Figure 5:
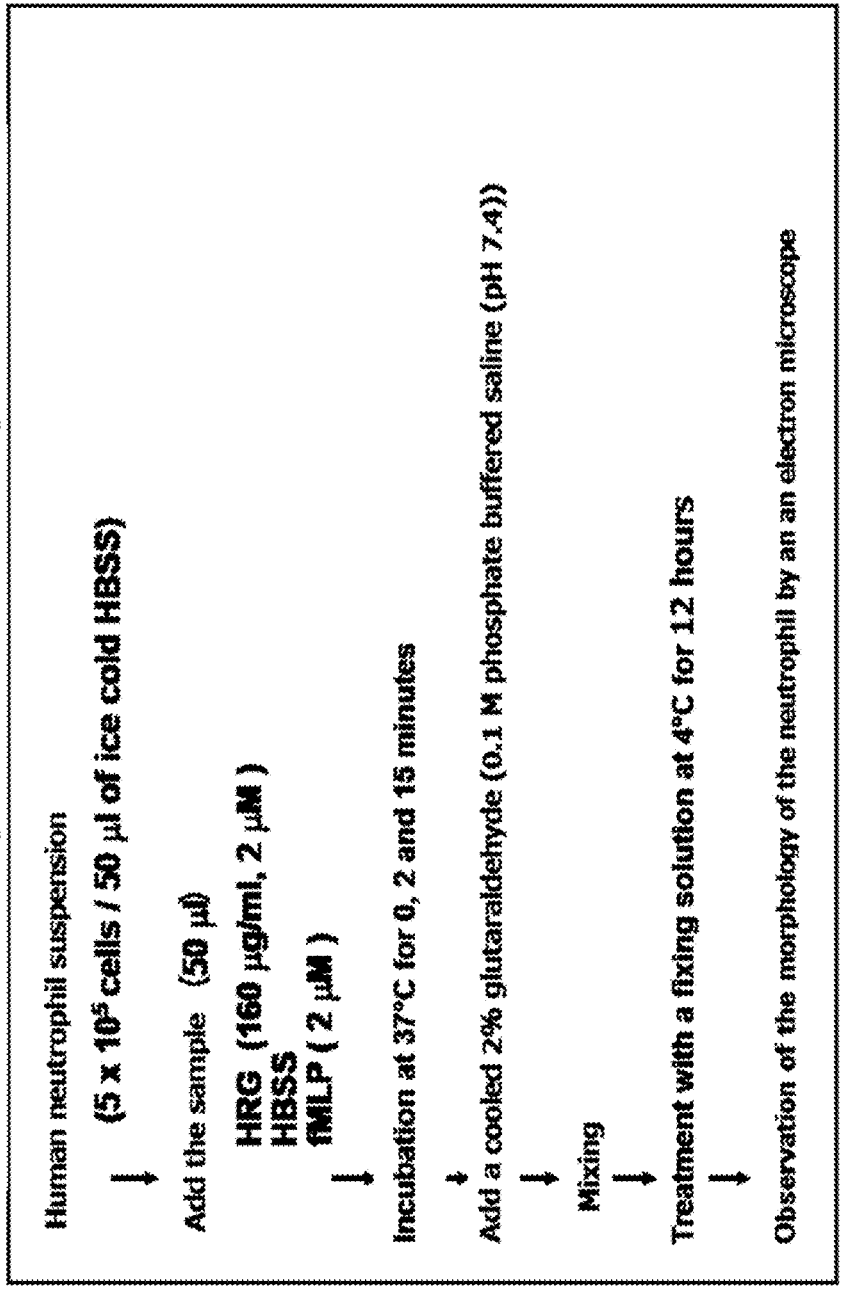
FIG. 5 A flow chart showing a processing method of the neutrophil for confirming the morphology of the neutrophil (Experimental Example 1-2).
Figure 6:
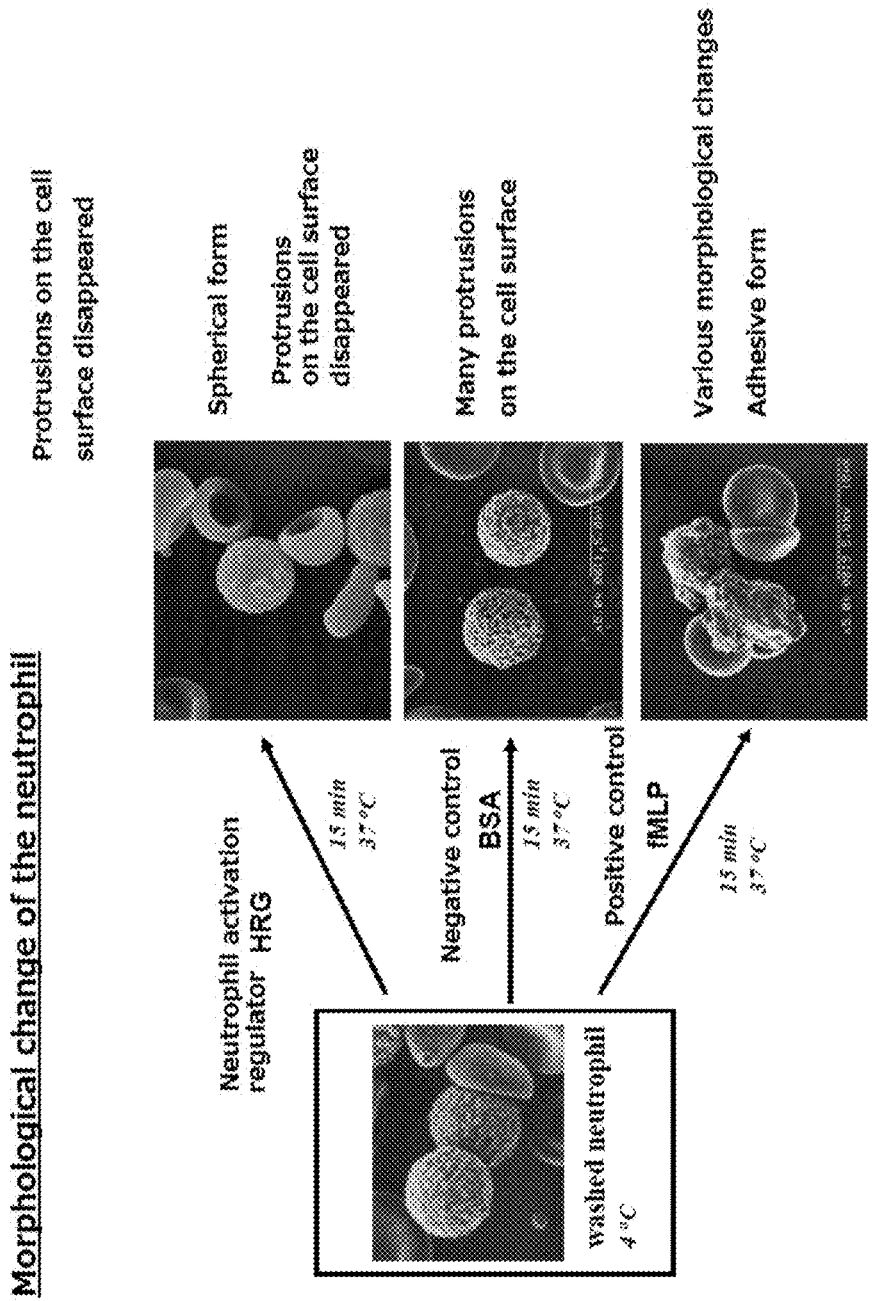
FIG. 6 Photographs taken in observing morphology of the neutrophil treated with HRG by an electron microscope. The positive control is fMLP, and the negative control is BSA (Experimental Example 1-2).

According to the flow chart shown in FIG. 5, the morphology of the neutrophil in the system in which 50 µl of neutrophil activation regulator prepared in Example 1 (HRG: 2 µM, final concentration: 1 µM) was added to 50 µl of neutrophil suspension prepared by the same procedure as in Experimental Example 1 (5×105 cell/ml) was observed by an electron microscope. In the same way as in Experimental Example 1, BSA was used as a negative control, and fMLP was used as a positive control. As a result, as shown in FIG. 6, it was observed that the positive control (fMLP) showed various morphological changes and an adhesive form, whereas the system with the neutrophil activation regulator (HRG) showed a more spherical state than that in the negative control (BSA). Also in the case of the negative control, many micro-villous protrusions appeared on the cell surface, and this was considered to be caused by stimulation by cell treatment, but in the system with neutrophil activation regulator, even when such a stimulation existed, activation of the neutrophil was controlled, and thus it was considered that a low activity state with extremely fewer micro-villous protrusions was able to be maintained.

Figure 7:
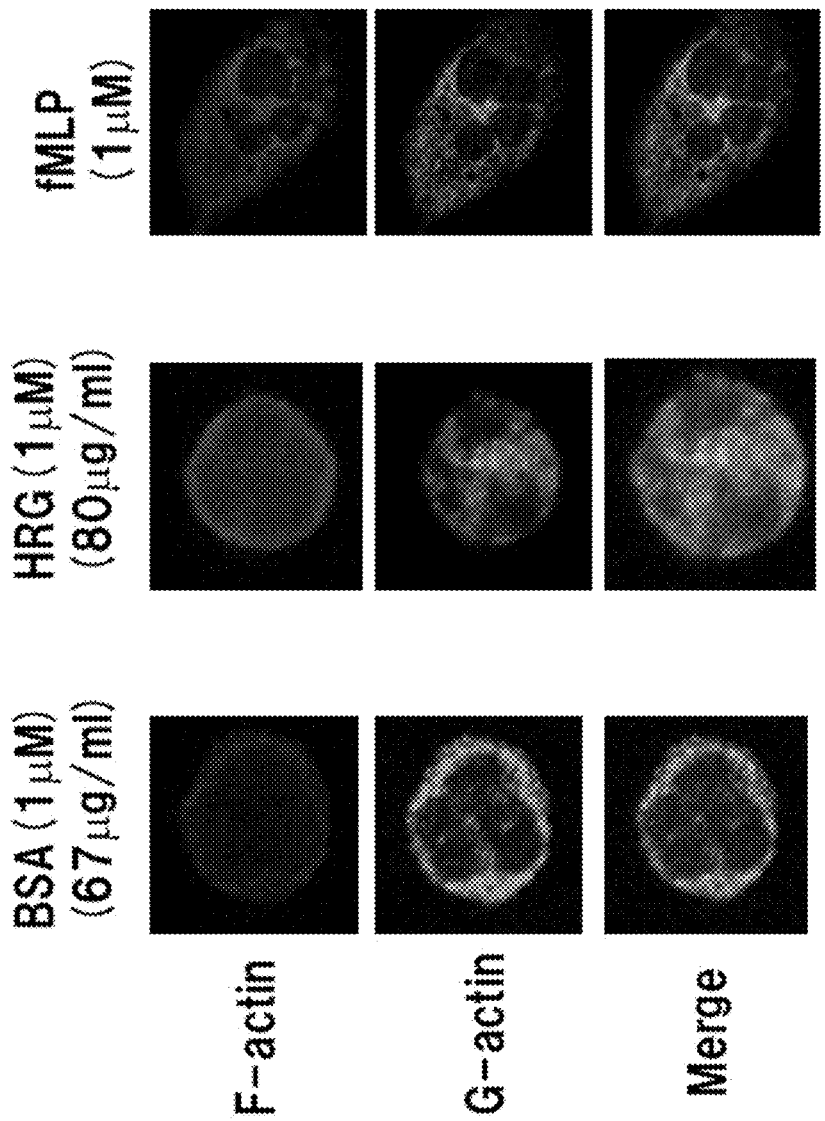
FIG. 7 Views taken in confirming distributions of F-actin and G-actin treated with HRG in neutrophils. The positive control is fMLP, and the negative control is BSA (Experimental Example 1-2).

Next, distributions of polymerized actins (F-actin) and globular actins (G-actin) in cells were observed. The F-actin was stained into red by Alexa Fluor 568-labeled phalloidin, and the G-actin was stained into green by Alexa Fluor 488-labeled deoxyribonuclease I. As a result, as shown in FIG. 7, it was observed that the neutrophil activation arranged the F-actin immediately below a plasma membrane of the cell.

Figure 8:
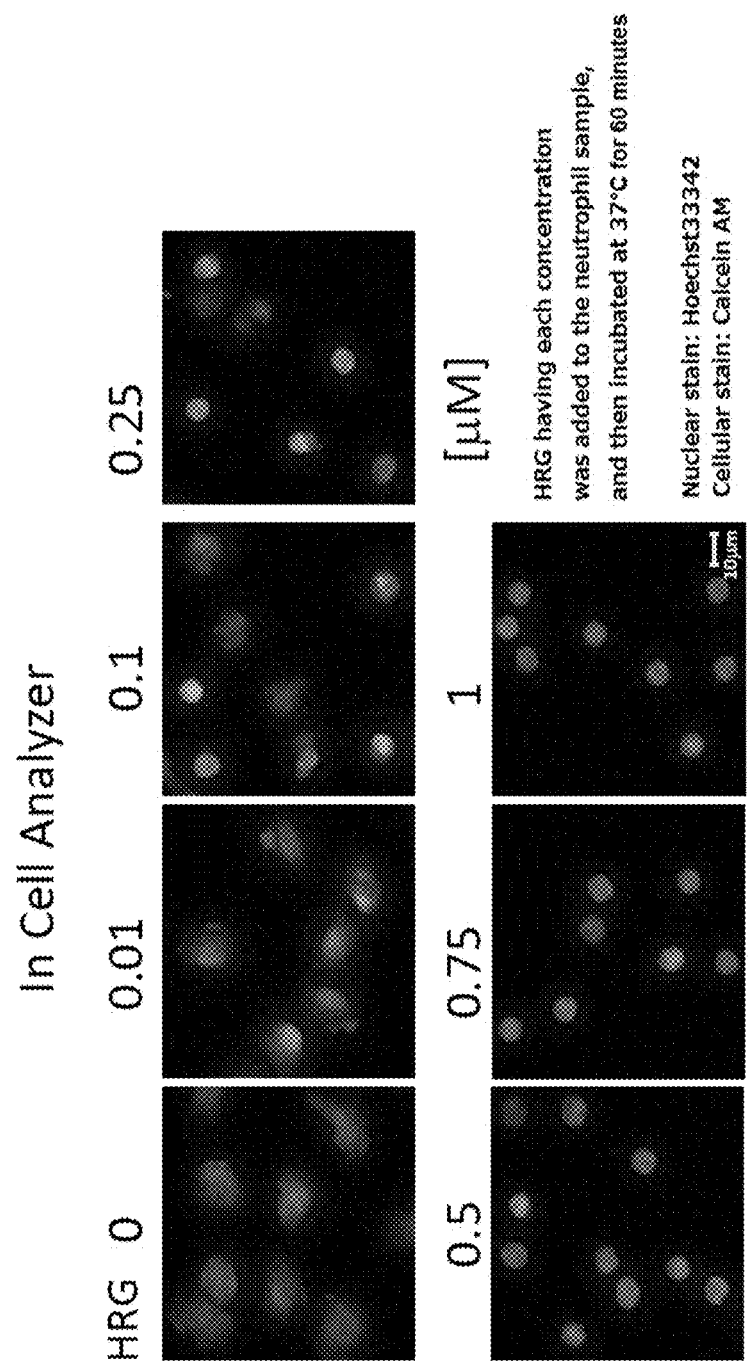
FIG. 8 Photographs taken in observing the morphology of the neutrophil treated with each concentration of HRG by cell fluorescence stain (Experimental Example 1-2).

Subsequently, the shapes of the cells in the system with the neutrophil activation regulator containing each concentration of HRG were confirmed with fluorescent label by using an imaging cytometer. As a result, it was observed that the cells were able to be maintained in a globular shape in a HRG concentration-dependent manner (FIG. 8).

Figure 9:
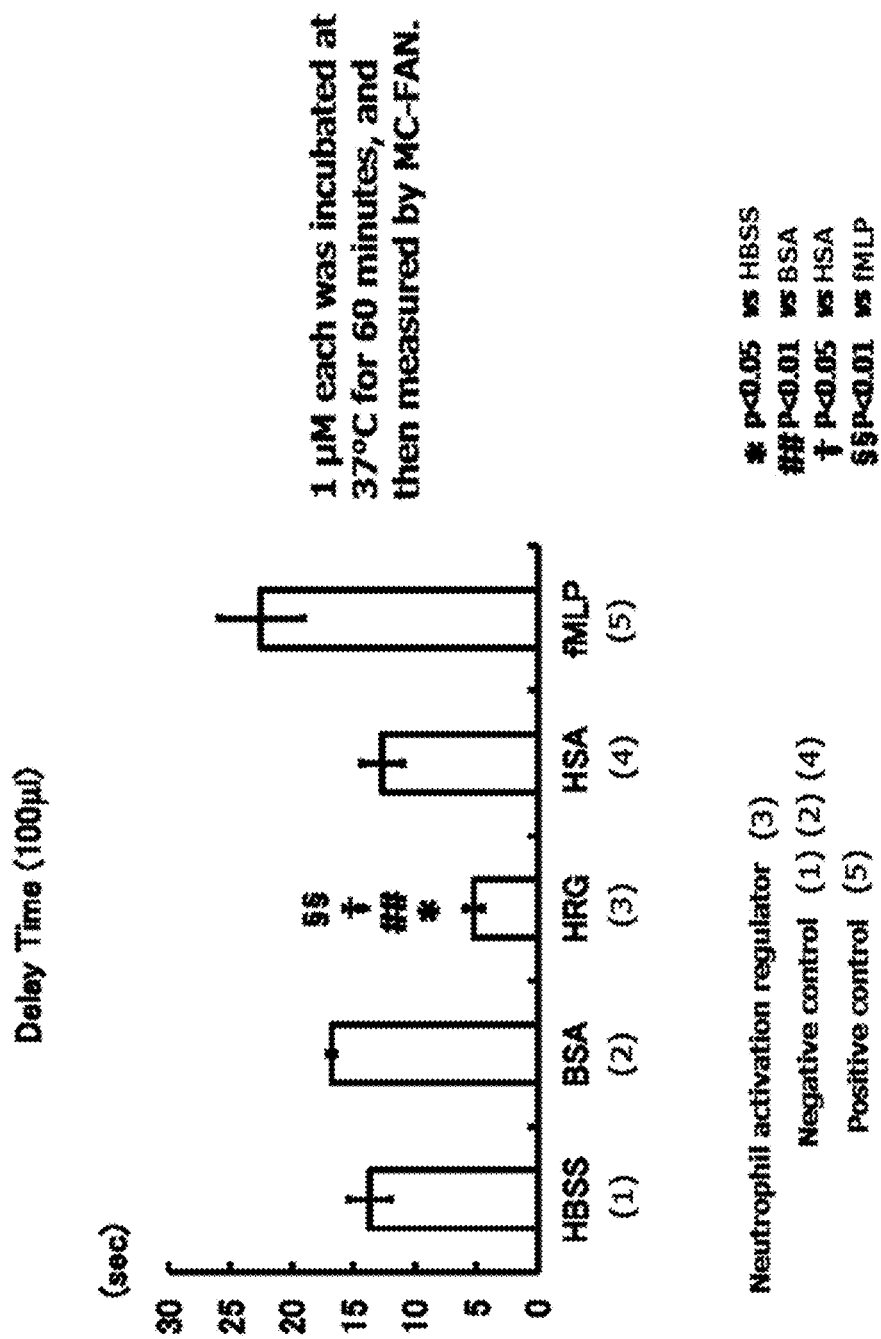
FIG. 9 Diagrams showing results of confirmation of flowability of the neutrophil suspension treated with HRG by MC-FAN. The positive control is fMLP, and the negative controls are BSA and HSA (Experimental Example 1-3).

(Experimental Example 1-3) Permeability of the Neutrophil Through an Artificial Capillary In this Experimental Example, a permeability of the neutrophil suspension by the neutrophil activation regulator (HRG: final concentration of 1 µM) prepared in Example 1 was measured by MC-FAN (Micro Channel array Flow Analyzer). The system in which the neutrophil activation regulator prepared in Example 1 was added to the neutrophil suspension was incubated at 37° C. for 60 minutes, and then its passage flowability was confirmed through measurement by using an MC-FAN silicon chip. The HBSS, BSA (bovine serum albumin) and HSA (human serum albumin) were used as negative controls, and the fMLP was used as a positive control. As a result, as shown in FIG. 9, the system of the neutrophil activation regulator showed smooth passage as compared with that of the negative control.

(Experimental Example 1-4) Adhesiveness of the Neutrophil

Figure 10:
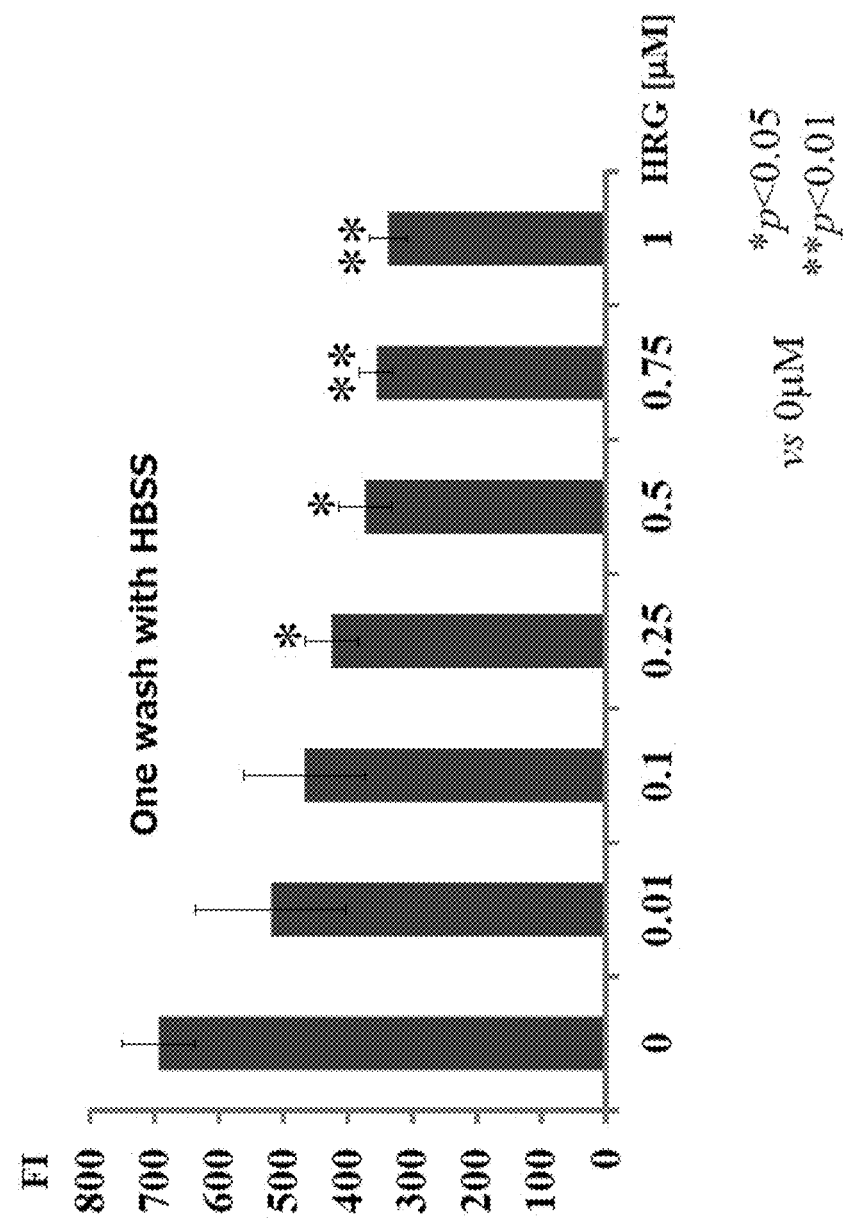
FIG. 10 Results of the number of the adherent cells in observing adhesion of the neutrophil to a microplate when the neutrophil was treated with each concentration of HRG (Experimental Example 1-4).

In this Experimental Example, after the neutrophil activation regulator containing each concentration of HRG prepared in Example 1 was added to the neutrophil suspension and incubated at 37° C. for 60 minutes, the adhesiveness of the neutrophil in the microplate was measured using the imaging cytometer. As a result, as shown in FIG. 10, it was confirmed that the system of the neutrophil activation regulator decreased the cell adhesiveness in a HRG concentration-dependent manner.

After that, the adhesiveness of the neutrophil to a human umbilical vein endothelial cell (HUVEC) was measured using the imaging cytometer. As a result, as shown in FIG. 11, it was confirmed that, in the system with the neutrophil activation regulator, the cell adhesiveness was maintained lower than that in the negative control.

(Example 2) Effects of the HRG on CLP Sepsis Model Mice

1. Change of the Blood HRG Level in CLP Model Mice.

In this Experimental Example, HRG kinetics was examined through the use of sepsis models with cecal ligation and puncture (CLP). A cecum was excised from an abdominal cavity of the mouse, the root of the cecum was ligated with a suture, and the layer of the cecal wall was punctured using an 18-gauge needle to produce a CLP sepsis model. A sham mouse was used a control. In relation to the blood HRG level in the living body, the plasma was subjected to SDS-PAGE electrophoresis, then transcribed on a nylon membrane, and detected by western blotting for measurement.

Figure 12:
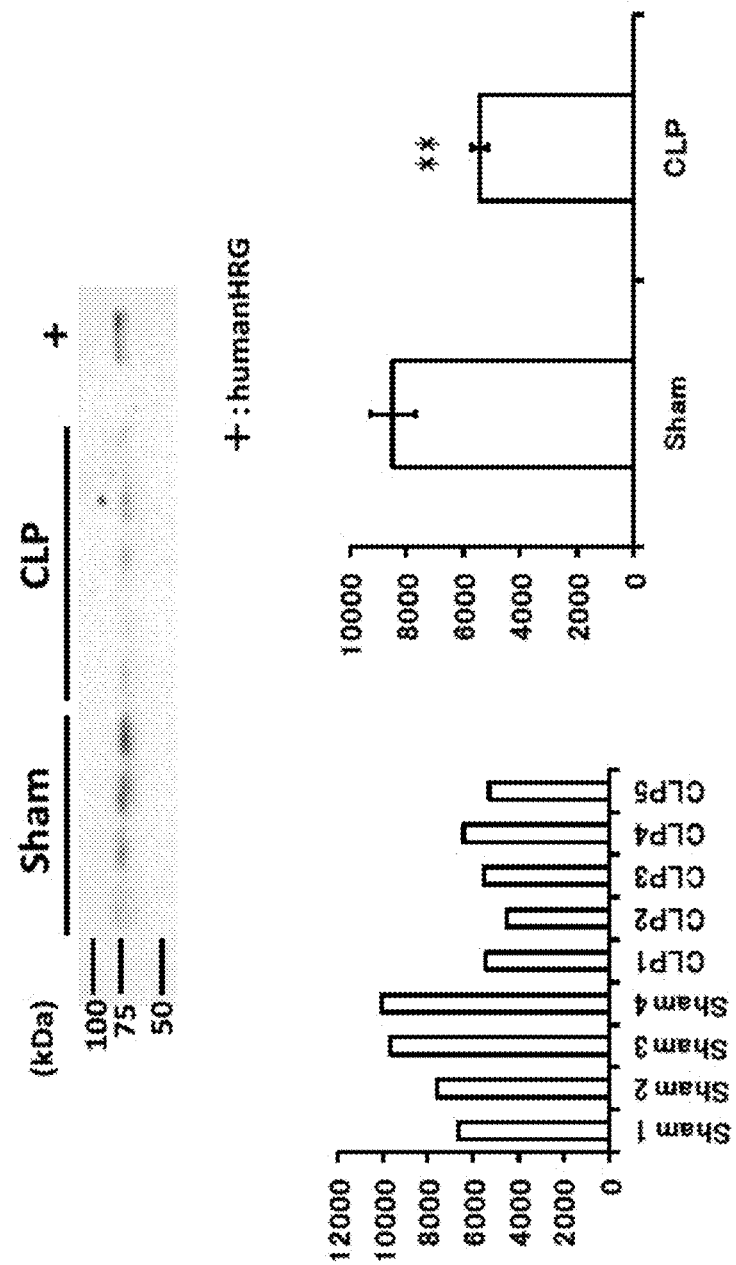
FIG. 12 Diagrams of results obtained by confirming the HRG kinetics in CLP sepsis model mice (Example 2).

As a result, it was observed that the HRG of the CLP sepsis model group was significantly decreased as compared with that of the sham group (FIG. 12).

2. Effects of the HRG on the CLP Sepsis Model Mice.

In this Example, effects on survival rates of mice when the neutrophil activation regulator prepared in Example 1 was administered to the CLP sepsis model mice produced by the same method as mentioned above were confirmed. The prepared neutrophil activation regulator (HRG: 400 μg/mouse) was administered into caudal vein, 5 minutes, 24 hours and 48 hours after the surgery (n=10). HSA was used as a control (n=10).

Figure 13:
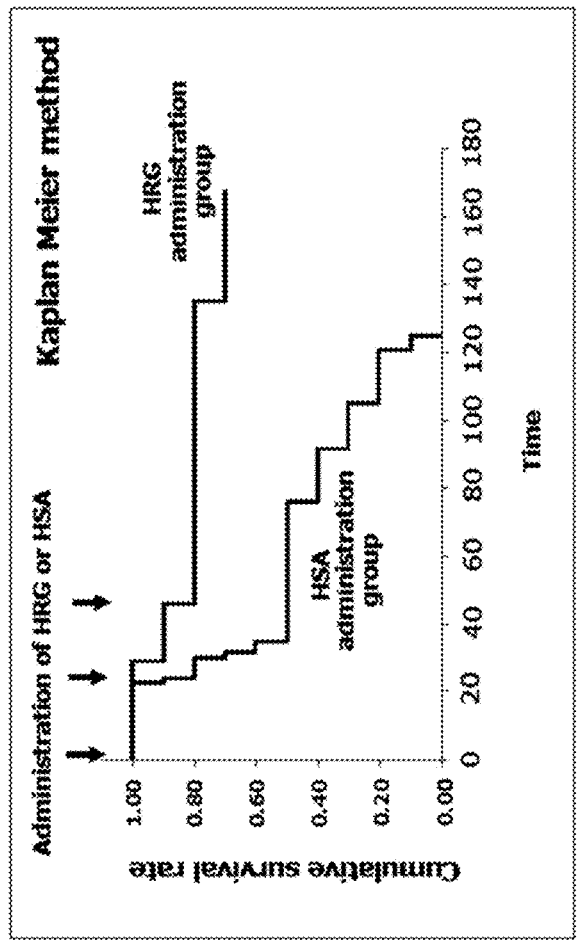
FIG. 13 Diagrams of results obtained by confirming the effects on the survival rates when the HRG was administered to the CLP sepsis model mice. The control is HSA (human serum albumin) (Example 2).

As a result of analysis by Kaplan Meier method, the group of neutrophil activation regulator administration was confirmed to have a significantly higher cumulative survival rate (FIG. 13).

(Example 3) Measurement Method for the HRG (Antibody Sandwich ELISA Method)

In this Example, a measurement method of the blood HRG by antibody sandwich ELISA (Enzyme-Linked ImmunoSorbent Assay) method will be explained.

By conventional method, rabbit immune serum immunized with human HRG was purified using Protein A to obtain an anti-human HRG-rabbit polyclonal antibody. For the HRG used in the immunization of the rabbit, a HRG prepared by the same procedure as described in Example 1 was used. To a plate for ELISA, 10 μl/ml (100 μl) of antibody solution adjusted with 0.05 M of Na2CO3 (pH 9.6) was added, and solid-phased at 4° C. for 16 hours. Subsequently, it was blocked with 3% BSA.

In this Example, an autogenous human HRG protein standard solution (native human HRG protein standard solution) made by the same procedure as in Example 1 was confirmed as a sample. Each concentration of native human HRG protein standard solution of 100 which was 200-500-fold diluted with Tris-Buffered Saline (TB S), was added and incubated at 37° C. for 2 hours. The plate for ELISA was washed with TBS, then 100 μl of HRP-labeled anti HRG-rat polyclonal antibody (clone #75-14) (0.25 μg/ml) was added, incubated at 37° C. for 1.5 hours. The plate for ELISA was washed with TBS, then ortho-phthalenediamine and H2O2 were added as substrates, chromogenic reaction was carried out for 30 minutes, then the reaction was terminated with 50 μl of 3M H2SO4, and an absorbance at 492 nm was measured.

Figure 14:
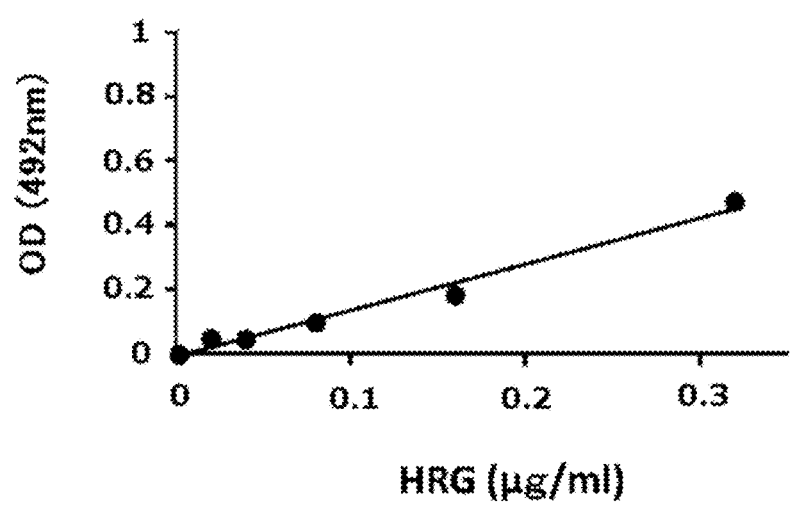
FIG. 14 A diagram showing results of measurement of a standard product (native human HRG protein standard solution) by an antibody sandwich ELISA method (Example 3).

The result of measurement for the native human HRG protein standard solution measured by the above-mentioned method is shown in FIG. 14.

(Example 4) Measurement Method for the HRG (Antibody/NiNTA-HRP Probe Sandwich ELISA Method)

In this Example, a measurement method for the blood HRG by an antibody/NiNTA-HRP probe sandwich ELISA method will be explained.

In this method, the rat monoclonal antibody (clone #75-14) was used as an antibody for capturing antigens. To the plate for ELISA, 10 μg/ml (100 μl) of monoclonal antibody solution adjusted with 0.05 M Na2CO3 (pH 9.6) was added, and solid-phased. Subsequently, it was blocked with 3% BSA, then each concentration of native human HRG protein standard solution of 100 μl, which was 200-500-fold diluted with TBS like in Experimental Example 3, was added and incubated at 37° C. for 2 hours. The plate was washed, then 100 μl of NiNTA-HRP probe (QUIAGEN Cat no. 34530, Tokyo, Japan) (0.25 μg/ml) was added, and incubated at 37° C. for 1.5 hours. The plate was washed, then ortho-phthalenediamine and $H_2O_2$ were added as substrates, chromogenic reaction was carried out for 30 minutes, then the reaction was terminated with 50 μl of 3M $H_2SO_4$, and an absorbance at 492 nm was measured.

Figure 15:
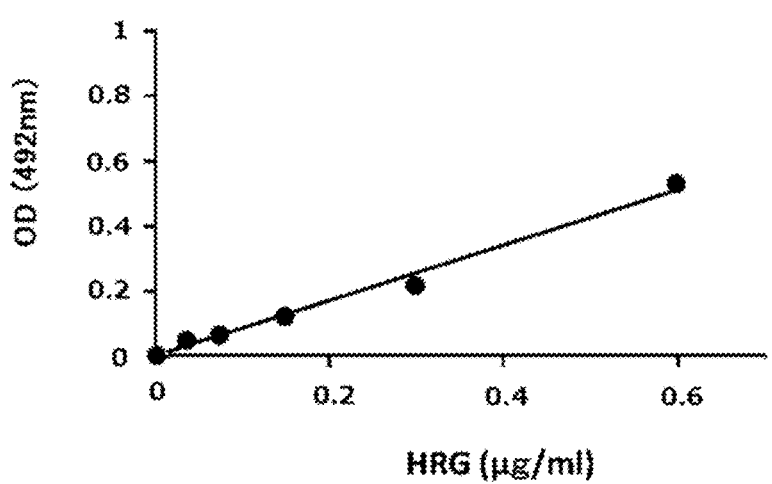
FIG. 15 A diagram showing results of measurement of a standard product (native human HRG protein standard solution) by an antibody/NiNTA-HRP probe sandwich ELISA method (Example 4).

The result of measurement for the native human HRG protein standard solution measured by the above-mentioned method is shown in FIG. 15.

(Example 5) Measurement Method for the HRG (Western Blot Method)

In this Example, a measurement method for the blood HRG by a western blot method will be explained. For the blood HRG, a collected human blood was added to a test tube with EDTA, a protease inhibitor cocktail (Sigma, P8340) was added to plasma obtained by centrifugation, and then measured as a sample for electrophoresis. Said adjusted plasma was subjected to SDS-PAGE according to a conventional method, and transcribed on a nitrocellulose membrane. The nitrocellulose membrane was blocked with 3% skim milk, and then reacted with the anti-human HRG-rabbit polyclonal antibody (2 μg/ml) as a primary antibody prepared by the same procedure as in Example 3 at 4° C. for 16 hours. The nitrocellulose membrane was washed, then 1 μg/ml of HRP-labeled anti rabbit IgG goat IgG was added as secondary antibody, and incubated at 37° C. for 1 hour. The nitrocellulose membrane was washed, then luminous reaction was carried out using Super Signal® West Dura Extended Duration Substrate (Thermo Scientific) as a substrate, and the HRG was detected by Lumino Image Analyzer (Image Quant Las 4000 mini, GE healthcare).

(Example 6) Blood HRG Level in Human Patients with Sepsis, Patients after Esophageal Cancer Surgery and Healthy Persons For plasma obtained from human patients with sepsis (3 persons), patients after esophageal cancer surgery (4 persons) and healthy persons (4 persons), the blood HRG was measured by the ELISA method described in Example 4 and the western blot method described in Example 5. Each plasma was prepared according to the method described in Example 5.

Figure 16:
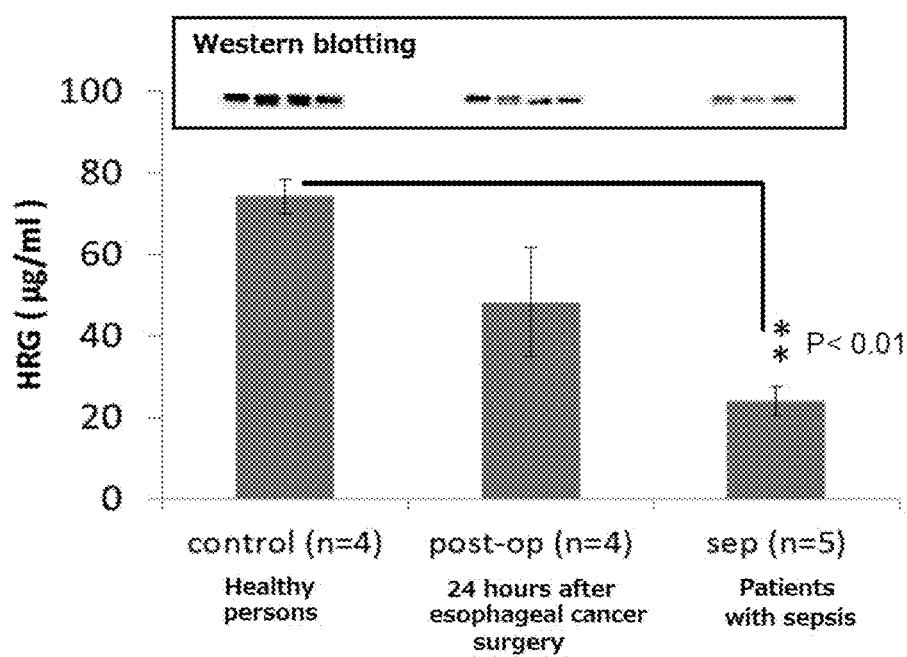
FIG. 16 A diagram showing results of western blotting and ELISA measurement for the blood HRG level in human patients with sepsis, patients after esophageal cancer surgery and healthy persons (Example 6).

Results of measurements are shown in FIG. 16. The results of measurement by the ELISA method are represented by a bar graph, and images of bands obtained by the western blot method are shown above the bar graph. As a result, the results of measurements by the western blotting and the ELISA method exhibited substantially the same result, and in the patients with sepsis, the blood HRG was confirmed to be significantly decreased as compared with that of the healthy persons.

(Example 7) Time Course of the Blood HRG in Acute Pancreatitis-ARDS Model Mice

In this Example, time courses of the blood HRG in model mice with acute pancreatitis due to caerulein and subsequent ARDS (acute respiratory distress syndrome) were confirmed. For causing acute pancreatitis and ARDS, mice (body weight 25-30 g) were intravenously injected with 100 μg/dose of caerulein seven times at intervals of one hour to produce model mice. Blood was collected with time after administration of caerulein, the HRG was measured for plasma prepared by the procedure in Example 5 by the western blot method.

Figure 17:
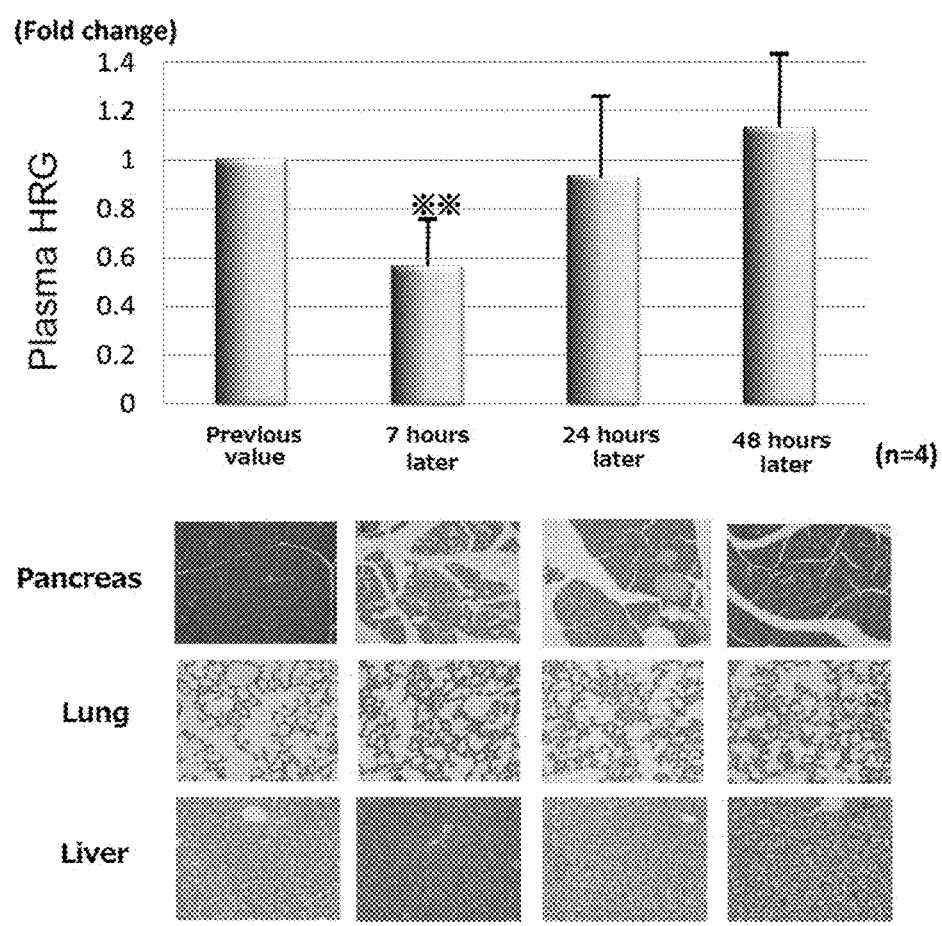
FIG. 17 Diagrams showing time course of the blood HRG and tissue images of pancreas, lung and liver after each lapse of time in acute pancreatitis-ARDS model mice. (Example 7)

Results of measurement are shown in FIG. 17. Also in the mouse acute pancreatitis-ARDS models, the blood HRG was confirmed to be significantly decreased like the mouse sepsis models in Example 2 and the human sepsis patients in Example 6. Furthermore, the tissue images of pancreas, lung and liver after each lapse of time were also confirmed. The blood HRG level was significantly decreased immediately after 7 administrations of caerulein (7 hours later), and recovery was achieved in 24 hours. The inflammation accompanied by edema of pancreas tissue stroma was most intense 7 hours later, and turned into recovery in 48 hours. The inflammation of lung was considered to be ARDS following pancreatitis, and persisted for 7 to 48 hours. In the liver, 24 hours later, vacuolization became remarkable, but 48 hours later, it was partially recovered.

(Example 8) Evaluation of Pneumonia and Effects of HRG Treatment in Sepsis-ARDS Model Mice In this Example, in relation to the model mice produced with CLP by the same procedure as described in Example 2, each pathology of ARDS when the neutrophil activation regulator (HRG) prepared in Example 1 was administrated was evaluated 24 hours after the surgery.

In mice that underwent deep anesthesia by intraperitoneal administration of pentobarbital, blood was removed in a transcardiac manner, systemic perfusion with saline was carried out, then lung tissues were excised, and whole RNA was extracted. A cDNA was synthesized by a reverse transcriptase, and then through the use of this as a template, mRNA expression of the following 5 inflammation-associated genes (TNF-α, PAI-1, Neutrophil elastase, IL-6, iNOS) and GAPDH was quantified and evaluated by Real-time PCR.

Figure 18:
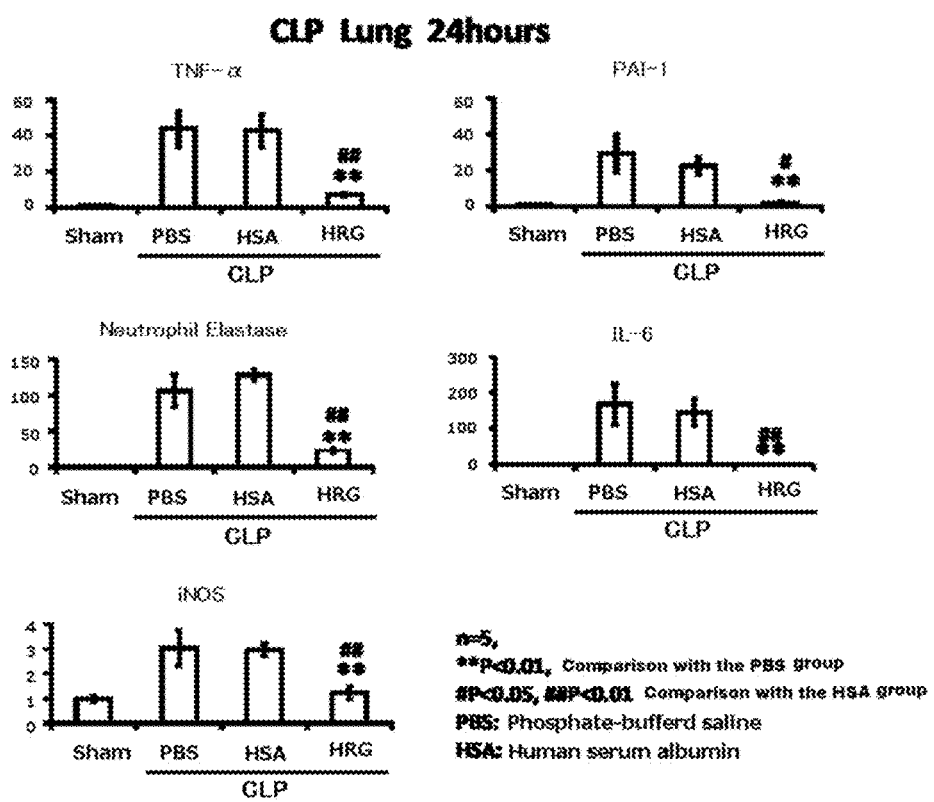
FIG. 18 Diagrams showing results of expressions of five inflammation-associated genes in lung tissues of sepsis-ARDS model mice. (Example 8)

Results of measurement are shown in FIG. 18. Although all expressions of the 5 genes in lung tissues of the sepsis-ARDS model mice were remarkably increased, it was confirmed that all the increased expressions were significantly inhibited by intravenous administration of 1.6 mg/kg of HRG. These results indicate considerable effectiveness of the HRG administration on septic ARDS.

(Example 9) Morphology of the Neutrophil in a Case of Treatment with a Recombinant Human HRG In this Example, effects on the morphology of the neutrophil in a case of treatment with the neutrophil activation regulator including a recombinant human HRG produced by a gene recombination procedure as an active ingredient will be explained.

1. Preparation of the Neutrophil Activation Regulator Including the Recombinant Human HRG as an Active Ingredient.

The recombinant human HRG was produced as below. A DNA encoding a human HRG-coding region (DNA made up of base sequences identified by GenBank Accession No. NM000412) was ligated into a plasmid vector having CMV promoter to prepare a vector for producing a recombinant human HRG. HEK293 cell (derived from human embryonic kidney cell, a transformant caused by adenovirus type 5) was seeded on a cell culture dish with 3.5×106 cells/10 cm diameter, and cultured. The cultured HEK293 cell was removed by a scraper, suspended, then a mixture of the vector for producing the recombinant human HRG 25 μg/OPTI-MEM 500 μl+FuGENE-HD 50 μl/OPTI-MEM 500 μl was added, and reacted at room temperature for 15 minutes for transfection. Subsequently, HEK293 cell was cultured at 37° C. under 5% CO2 for 48 hours to produce the recombinant human HRG.

A culture supernatant containing the recombinant human HRG was collected, and filtrated by a filter with a pore size of 0.22 QIAGEN® Ni-NTA agarose gel (gel in which Ni-NTA binds to Sepharose CL-6B support) previously washed with 30 ml of 1×PBS(-) was added to said filtrated culture supernatant and incubated while rotating at 4° C. for 1 hour to combine the recombinant human HRG to QIAGEN® Ni-NTA agarose gel. QIAGEN® Ni-NTA agarose gel was transferred to a purification column, and then the column was washed with a wash fluid 1 (PBS containing 30 mM Imidazole (pH 7.4)), a wash fluid 2 (1M NaCl+10 mM PBS (pH 7.4)) and a wash fluid 3 (1×PBS (pH 7.4)) sequentially. The recombinant human HRG was eluted by reaction with PBS containing 500 mM Imidazole (pH 7.4) at 4° C. for 1 hour. In the purified product, the HRG was confirmed by western blotting and protein stain after SDS-PAGE.

2. Morphology of the Neutrophil.

Figure 19:
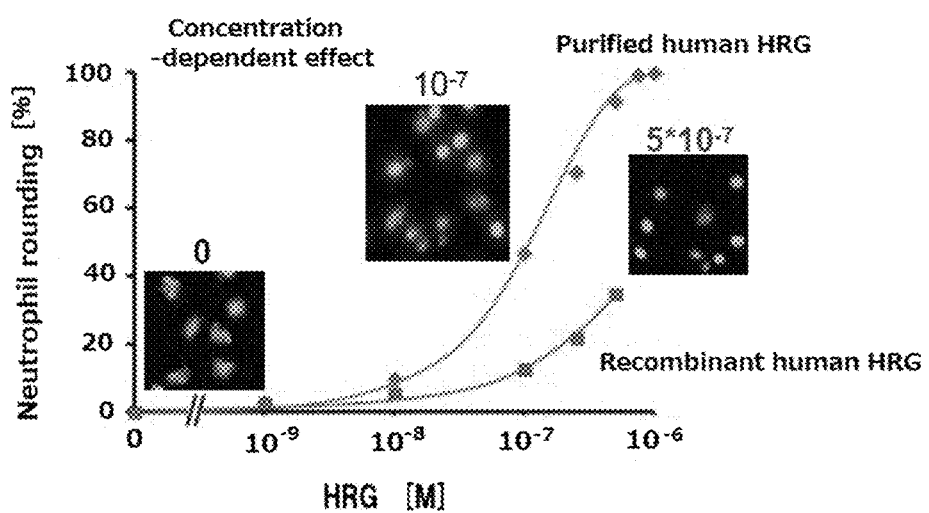
FIG. 19 A diagram showing results obtained by observing the morphology of the neutrophil by a fluorescence microscope and confirming the spherical shape change of the neutrophil when each concentration of recombinant human HRG or human plasma-derived HRG was activated. (Example 9)
Figure 20:
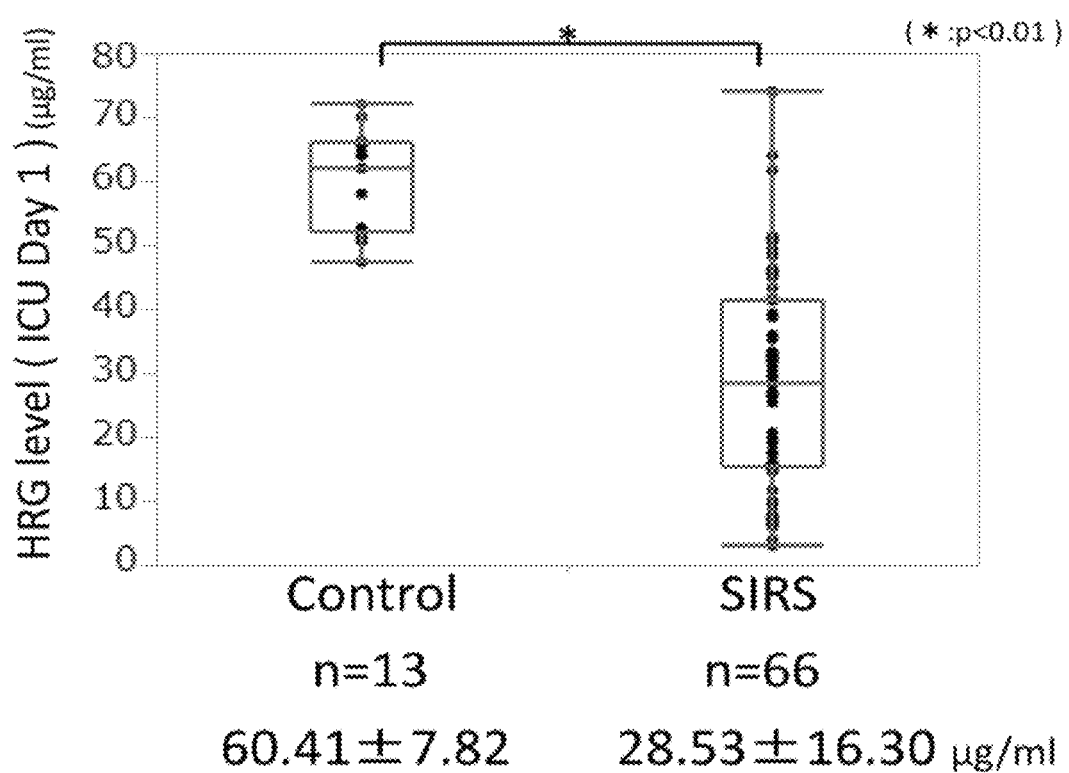
FIG. 20 Diagram showing the levels of HRG in the blood of healthy volunteers and SIRS patients. (Example 10)
Figure 21:
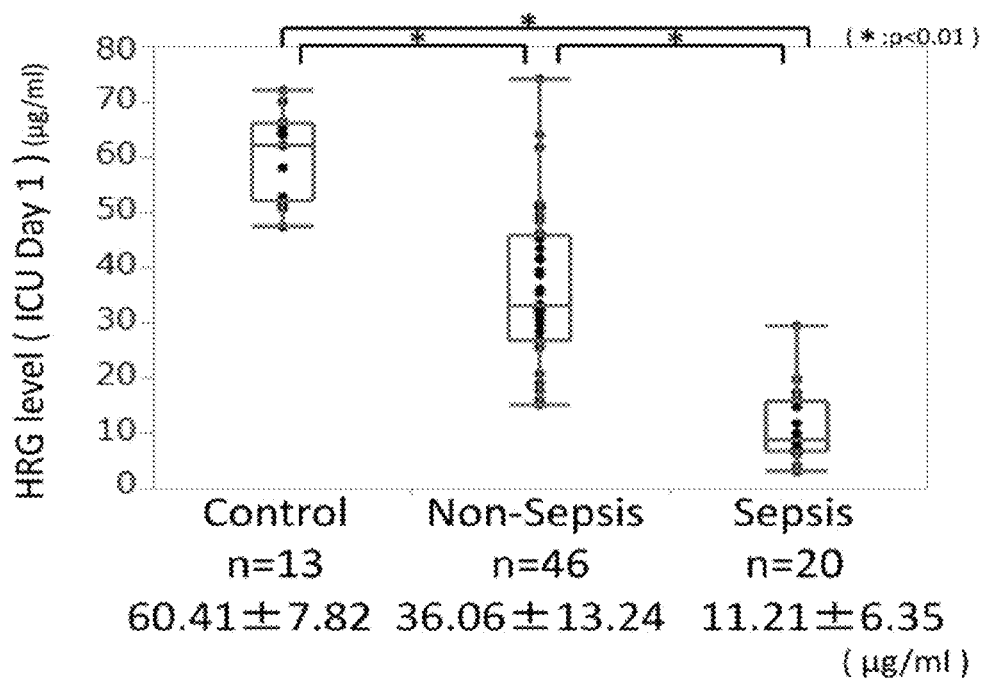
FIG. 21 Diagram showing the levels of HRG in the blood of healthy volunteers, SIRS patients with no sepsis infection, and SIRS patients with sepsis infection. (Example 10)
Figure 22:
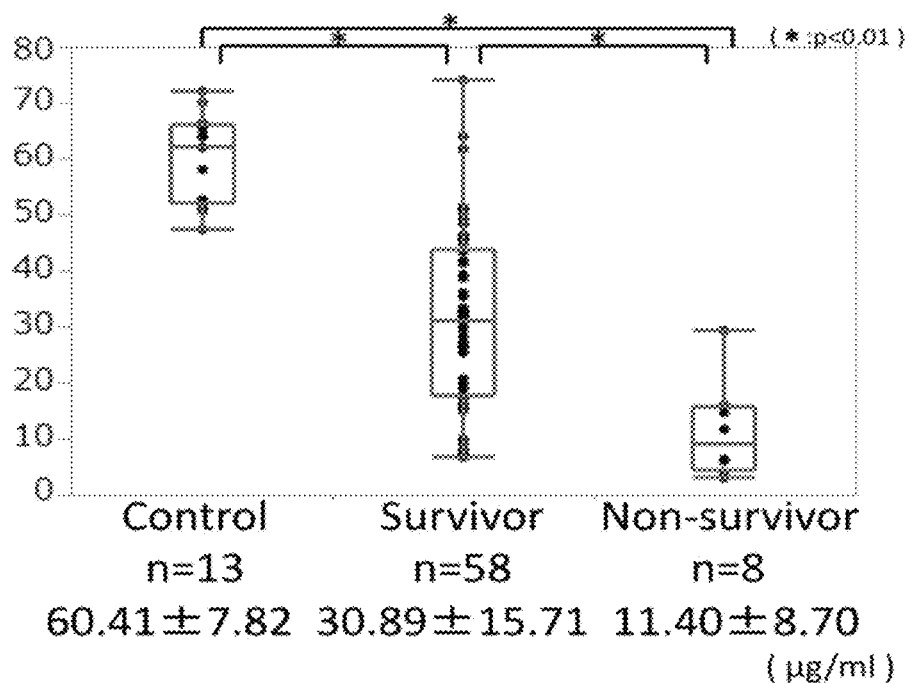
FIG. 22 Diagram showing the levels of HRG in the blood of healthy volunteers, SIRS survivors, and SIRS non-survivors. (Example 10)

A protein concentration was adjusted by HBSS substitution of the recombinant human HRG purified product, and spherical shape—inducing activity of human neutrophil when each concentration of recombinant human HRG was activated was assayed by the same procedure as described in the Experimental Example 1-2. For comparison, the human plasma-derived HRG produced in Example 1 was also confirmed. The results are shown in FIG. 19. Although the activity of the recombinant human HRG was lower than of the human plasma-derived HRG, it was observed that the cells were able to be maintained in the globular shape in a HRG concentration-dependent manner.

Example 10: Histidine-Rich Glycoprotein (HRG) is an Effective Prognostic Biomarker in Critically ID Patients Description of the Study Sepsis is a systemic illness and represents one of the most severe diseases in patients in intensive care unit. The aim of the study was to assess the levels of HRG in critically ill SIRS patients and determine the relationship between HRG levels and mortality in those patients. Blood samples were collected from the patients within 24 hours of their admission to the intensive care unit, and HRG levels were determined in the plasma by quantitative ELISA. Detection was performed by affinity chromatography using Ni-NTA-HRP conjugate. For comparison, blood samples were also collected from healthy volunteers and analyzed. The data were expressed as means±standard deviations. Student t-test and ANOVA were used for comparison between the groups. Logistic regression models and Cox proportional hazard model were also applied to analyze the relationship between HRG levels and mortality.

Results

Figure 23:
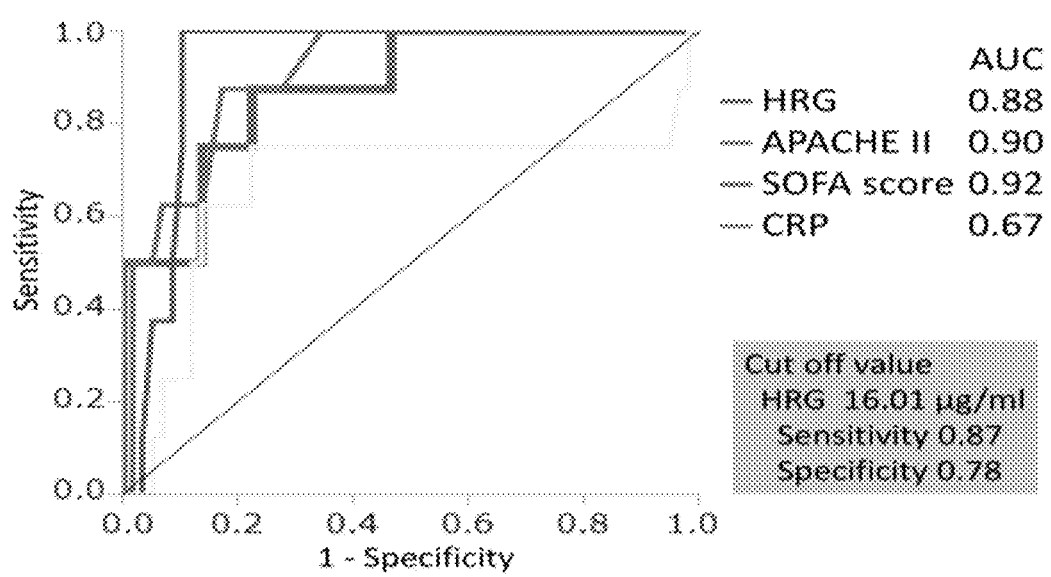
FIG. 23 Plot showing the receiver operator characteristics (ROC) analysis of levels of HRG for mortality. The cutoff value was 16.01 µg/ml and the areas under the curve (AUC) were 0.88. (Example 10)
Figure 24:
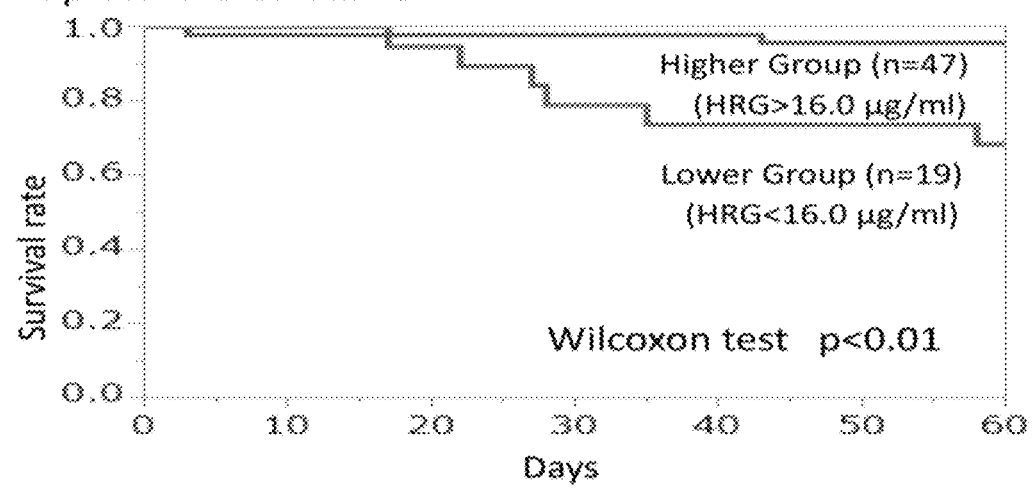
FIG. 24 Plot showing the survival rate for patients above and below the cutoff value of 16.01 µg/ml. The patients with a lower level of HRG showed significantly higher mortality. (Example 10)

The HRG levels in the plasma of SIRS patients (n=66) were significantly lower compared to the HRG levels in healthy volunteers (n=13) (28.53±16.30 vs. 60.41±7.82 μg/ml; p<0.01). The HRG levels in the plasma of SIRS patients having an infection (n=20) were significantly lower than those in SIRS patients not having an infection (n=46) (11.21±6.35 vs. 36.06±13.24 μg/ml; p<0.01). Moreover, the HRG levels in the plasma of non-survivors (n=8) were significantly lower than those in survivors (n=58) (11.40±8.70 vs. 30.89±15.71 μg/ml; p<0.01). In univariate analysis, the HRG levels were correlated with mortality (Odd ratio 0.86; p<0.01). The receiver operator characteristics (ROC) curve analysis of HRG levels for mortality revealed that the cutoff value was 16.01 μg/ml and the areas under the curve (AUC) were 0.88. Furthermore, when patients were divided into two groups according to their HRG levels using the cutoff value of 16.01 μg/ml, the lower HRG group showed significantly higher mortality (Hazard ratio 8.44; p<0.01) (FIG. 23). The correlation between HRG level and mortality is shown in the table below.

|  | Odd Ratio | 95% C.I. | P value | Adjusted OR | 95% C.I. | P Value |
|---|---|---|---|---|---|---|
| HRG Level | 0.86 | 0.76-0.94 | <0.01* | 0.90 | 0.78-0.98 | 0.024* |
| Apache II score | 1.22 | 1.09-1.41 | <0.01* | 1.13 |  | 0.022* |
| SOFA score | 1.41 | 1.17-1.78 | <0.01* |  |  |  |
| CRP Level | 1.11 | 1.00-1.23 | <0.01* |  |  |  |

CONCLUSION

These results demonstrate that the HRG levels in the plasma of SIRS patients were significantly low. HRG levels in septic SIRS patients were even lower than those in non-septic SIRS patients. The data additionally show that the HRG levels were correlated with survival and mortality. These results indicate that HRG is an effective prognostic biomarker in septic patients.

INDUSTRIAL APPLICABILITY

As detailed above, by using the neutrophil activation regulator including the HRG of the present invention as an active ingredient, the neutrophil-vascular endothelial cell interaction can be inhibited, for example, diseases caused by neutrophil activation and/or inflammatory diseases accompanied by neutrophil activation can be treated. In addition, since the diseases caused by neutrophil activation and/or the inflammatory diseases accompanied by neutrophil activation decrease blood HRG level, the diseases caused by neutrophil activation and/or the inflammatory diseases accompanied by neutrophil activation can be tested by measuring the HRG.

The invention claimed is:

1. A method for determining the severity of and treating a systemic inflammatory response syndrome (SIRS) in a subject in need thereof, comprising:
   collecting a blood sample from the subject;
   separating and purifying a plasma-enriched fraction from the blood sample;
   measuring a level of an endogenous histidine-rich glycoprotein in the plasma-enriched fraction;
   determining severe SIRS when the level of the endogenous histidine-rich glycoprotein is below 30 µg/ml in the plasma-enriched fraction; and
   administering to the subject a composition comprising an exogenous histidine-rich glycoprotein and an aqueous or non-aqueous carrier to decrease the severity of the SIRS.

2. The method according to claim 1, wherein the level of the endogenous histidine-rich glycoprotein is measured by an immunological technique.

3. The method according to claim 2, wherein the immunological technique is quantitative ELISA, and wherein the endogenous histidine-rich glycoprotein is detected by nickel-nitrilotriacetic acid (Ni-NTA) affinity.

4. The method according to claim 1, wherein the systemic inflammatory response syndrome (SIRS) is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

5. The method according to claim 1, wherein the systemic inflammatory response syndrome (SIRS) is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, hepatitis, organ dysfunction after surgical operation, acute/chronic rejection after organ transplantation, DIC, endocarditis, ischemia reperfusion disorder, myocardial infarction and congestive heart failure.

6. A method for predicting the survival of and treating a subject with systemic inflammatory response syndrome (SIRS) comprising:
   collecting a blood sample from the subject;
   separating and purifying a plasma-enriched fraction from the blood sample;
   measuring the level of an endogenous histidine-rich glycoprotein in the plasma-enriched fraction;
   determining poor survival when the level of the endogenous histidine-rich glycoprotein is below 30 µg/ml in the plasma-enriched fraction; and
   administering to the subject a composition comprising an exogenous histidine-rich glycoprotein and an aqueous or non-aqueous carrier to improve survival.

7. The method according to claim 6, wherein the level of the endogenous histidine-rich glycoprotein is measured by an immunological technique.

8. The method according to claim 7, wherein the immunological technique is quantitative ELISA, and wherein the histidine-rich glycoprotein is detected by nickel-nitrilotriacetic acid (Ni-NTA) affinity.

9. The method according to claim 6, wherein the systemic inflammatory response syndrome (SIRS) is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, cerebral trauma, spinal cord injury, neuropathic pain, cerebral infarction, cerebral vasospasm after the subarachnoid hemorrhage, epilepsy, status epilepticus, viral encephalitis, influenza-associated encephalopathy, inflammatory bowel disease, kawasaki disease, multiple sclerosis, diabetic vascular complication, hepatitis, arteriosclerosis, asthma bronchial, chronic bronchitis, pulmonary emphysema, organ dysfunction after surgical operation, organ dysfunction after radiotherapy, nephritis, nephrotic syndrome, acute renal failure, haemodialysis, extracorporeal circulation, artificial breathing, acute/chronic rejection after organ transplantation, SLE, rheumatoid arthritis, DIC, autoimmune disease group, Behcet's disease, myocarditis, endocarditis, ischemia reperfusion disorder, myocardial infarction, congestive heart failure, adipose tissue inflammation, neutrophilic dermatosis, Sweet's disease, Stevens-Johnson syndrome, Reye syndrome, cachexia, chronic fatigue syndrome and fibromyalgia.

10. The method according to claim 6, wherein the systemic inflammatory response syndrome (SIRS) is one or more of sepsis, acute respiratory distress syndrome, acute pancreatitis, acute pulmonary disorder, pulmonary disorder caused by the hemorrhagic shock, multiple organ failure, burn, multiple injury, idiopathic interstitial pulmonary fibrosis, hepatitis, organ dysfunction after surgical operation, acute/chronic rejection after organ transplantation, DIC, endocarditis, ischemia reperfusion disorder, myocardial infarction and congestive heart failure.

11. The method of claim 1, wherein the composition administered further comprises an antimicrobial compound, an antioxidant, a chelating agent, an inert gas, or any combination thereof.

12. The method of claim 1, wherein the composition further comprises one or more additional drugs.

13. The method of claim 1, wherein the composition further comprises an anti-HMGB1 monoclonal antibody.

14. The method of claim 6, wherein the composition administered further comprises an antimicrobial compound, an antioxidant, a chelating agent, an inert gas, or any combination thereof.

15. The method of claim 6, wherein the composition further comprises one or more additional drugs.

16. The method of claim 6, wherein the composition further comprises an anti-HMGB1 monoclonal antibody.

* * * * *

SEQUENCE LISTING

<160> NUMBER OF SEQ ID NOS: 2

<210> SEQ ID NO 1
<211> LENGTH: 507
<212> TYPE: PRT
<213> ORGANISM: Homo sapiens

<400> SEQUENCE: 1

Val Ser Pro Thr Asp Cys Ser Ala Val Glu Pro Glu Ala Glu Lys Ala
1               5                   10                  15

Leu Asp Leu Ile Asn Lys Arg Arg Arg Asp Gly Tyr Leu Phe Gln Leu
            20                  25                  30

Leu Arg Ile Ala Asp Ala His Leu Asp Arg Val Glu Asn Thr Thr Val
        35                  40                  45

Tyr Tyr Leu Val Leu Asp Val Gln Glu Ser Asp Cys Ser Val Leu Ser
    50                  55                  60

Arg Lys Tyr Trp Asn Asp Cys Glu Pro Pro Asp Ser Arg Arg Pro Ser
65                  70                  75                  80

Glu Ile Val Ile Gly Gln Cys Lys Val Ile Ala Thr Arg His Ser His

```
                         85                  90                  95
Glu Ser Gln Asp Leu Arg Val Ile Asp Phe Asn Cys Thr Thr Ser Ser
                100                 105                 110
Val Ser Ser Ala Leu Ala Asn Thr Lys Asp Ser Pro Val Leu Ile Asp
                115                 120                 125
Phe Phe Glu Asp Thr Glu Arg Tyr Arg Lys Gln Ala Asn Lys Ala Leu
                130                 135                 140
Glu Lys Tyr Lys Glu Gly Asn Asp Asp Phe Ala Ser Phe Arg Val Asp
145                 150                 155                 160
Arg Ile Glu Arg Val Ala Arg Val Arg Gly Gly Glu Gly Thr Gly Tyr
                165                 170                 175
Phe Val Asp Phe Ser Val Arg Asn Cys Pro Arg His His Phe Pro Arg
                180                 185                 190
His Pro Asn Val Phe Gly Phe Cys Arg Ala Asp Leu Phe Tyr Asp Val
                195                 200                 205
Glu Ala Leu Asp Leu Glu Ser Pro Lys Asn Leu Val Ile Asn Cys Glu
                210                 215                 220
Val Phe Asp Pro Gln Glu His Glu Asn Ile Asn Gly Val Pro Pro His
225                 230                 235                 240
Leu Gly His Pro Phe His Trp Gly Gly His Glu Arg Ser Ser Thr Thr
                245                 250                 255
Lys Pro Pro Phe Lys Pro His Gly Ser Arg Asp His His His Pro His
                260                 265                 270
Lys Pro His Glu His Gly Pro Pro Pro Pro Asp Glu Arg Asp His
                275                 280                 285
Ser His Gly Pro Pro Leu Pro Gln Gly Pro Pro Leu Leu Pro Met
290                 295                 300
Ser Cys Ser Ser Cys Gln His Ala Thr Phe Gly Thr Asn Gly Ala Gln
305                 310                 315                 320
Arg His Ser His Asn Asn Asn Ser Ser Asp Leu His Pro His Lys His
                325                 330                 335
His Ser His Glu Gln His Pro His Gly His His Pro His Ala His His
                340                 345                 350
Pro His Glu His Asp Thr His Arg Gln His Pro His Gly His His Pro
                355                 360                 365
His Gly His His Pro His Gly His His Pro His Gly His His Pro His
                370                 375                 380
Gly His His Pro His Cys His Asp Phe Gln Asp Tyr Gly Pro Cys Asp
385                 390                 395                 400
Pro Pro Pro His Asn Gln Gly His Cys Cys His Gly His Gly Pro Pro
                405                 410                 415
Pro Gly His Leu Arg Arg Arg Gly Pro Gly Lys Gly Pro Arg Pro Phe
                420                 425                 430
His Cys Arg Gln Ile Gly Ser Val Tyr Arg Leu Pro Pro Leu Arg Lys
                435                 440                 445
Gly Glu Val Leu Pro Leu Pro Glu Ala Asn Phe Pro Ser Phe Pro Leu
                450                 455                 460
Pro His His Lys His Pro Leu Lys Pro Asp Asn Gln Pro Phe Pro Gln
465                 470                 475                 480
Ser Val Ser Glu Ser Cys Pro Gly Lys Phe Lys Ser Gly Phe Pro Gln
                485                 490                 495
Val Ser Met Phe Phe Thr His Thr Phe Pro Lys
                500                 505
```

```
<210> SEQ ID NO 2
<211> LENGTH: 5
<212> TYPE: PRT
<213> ORGANISM: Homo sapiens

<400> SEQUENCE: 2

Gly His His Pro His
1               5
```